(12) United States Patent
Zhang

(10) Patent No.: US 12,227,561 B2
(45) Date of Patent: Feb. 18, 2025

(54) CONNEXIN 43 ANTIBODIES AND USE THEREOF

(71) Applicant: AlaMab Therapeutics, Inc., Princeton, NJ (US)

(72) Inventor: Yanfeng Zhang, Princeton, NJ (US)

(73) Assignee: ALAMAB THERAPEUTICS, INC., Princeton, NJ (US)

( * ) Notice: Subject to any disclaimer, the term of this patent is extended or adjusted under 35 U.S.C. 154(b) by 927 days.

(21) Appl. No.: 17/045,001

(22) PCT Filed: Apr. 2, 2019

(86) PCT No.: PCT/US2019/025363
§ 371 (c)(1),
(2) Date: Oct. 2, 2020

(87) PCT Pub. No.: WO2019/195273
PCT Pub. Date: Oct. 10, 2019

(65) Prior Publication Data
US 2021/0163581 A1    Jun. 3, 2021

Related U.S. Application Data

(60) Provisional application No. 62/651,668, filed on Apr. 2, 2018.

(51) Int. Cl.
| C07K 16/00 | (2006.01) |
| A61K 39/395 | (2006.01) |
| A61P 35/00 | (2006.01) |
| C07K 16/18 | (2006.01) |
| C07K 16/28 | (2006.01) |
| C07K 16/46 | (2006.01) |
| A61K 39/00 | (2006.01) |

(52) U.S. Cl.
CPC ........ *C07K 16/18* (2013.01); *A61K 39/39533* (2013.01); *A61P 35/00* (2018.01); *C07K 16/28* (2013.01); *A61K 2039/505* (2013.01); *C07K 2317/33* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,740,461 A | 4/1988 | Kaufman | |
| 4,816,567 A | 4/1989 | Cabilly et al. | |
| 4,912,040 A | 3/1990 | Kaufman et al. | |
| 4,959,455 A | 9/1990 | Clark et al. | |
| 5,530,101 A | 6/1996 | Queen et al. | |
| 5,545,807 A | 8/1996 | Surani et al. | |
| 5,585,089 A | 12/1996 | Queen et al. | |
| 5,693,761 A | 12/1997 | Queen et al. | |
| 5,693,762 A | 12/1997 | Queen et al. | |
| 6,180,370 B1 | 1/2001 | Queen et al. | |
| 11,912,764 B2* | 2/2024 | Zhang | C07K 16/18 |
| 2004/0101920 A1 | 5/2004 | Radziejewski et al. | |
| 2005/0171339 A1 | 8/2005 | Sugo et al. | |
| 2009/0324602 A1* | 12/2009 | Garber | A61P 35/00 |
| | | | 424/139.1 |
| 2011/0223204 A1 | 9/2011 | Duft et al. | |
| 2012/0214234 A1 | 8/2012 | Takamatsu et al. | |
| 2015/0140021 A1 | 5/2015 | Kao et al. | |
| 2016/0177298 A1 | 6/2016 | Green et al. | |
| 2016/0200812 A1* | 7/2016 | Jiang | G01N 33/5032 |
| | | | 424/139.1 |
| 2016/0331805 A1 | 11/2016 | Green et al. | |
| 2019/0359696 A1* | 11/2019 | Jiang | C07K 16/18 |
| 2022/0411494 A1 | 12/2022 | Zhang | |

FOREIGN PATENT DOCUMENTS

| | | |
|---|---|---|
| EP | 0546073 B1 | 10/1997 |
| WO | 199004036 A1 | 4/1990 |
| WO | 199110741 A1 | 7/1991 |
| WO | 199402602 A1 | 2/1994 |
| WO | 199633735 A1 | 10/1996 |
| WO | 199910494 A2 | 3/1999 |
| WO | WO 2005/059106 A2 | 6/2005 |
| WO | WO 2009/140177 A2 | 11/2009 |
| WO | 2015027120 A1 | 2/2015 |
| WO | 2017025016 A1 | 2/2017 |
| WO | 2017147561 A1 | 8/2017 |
| WO | 2019195273 A1 | 10/2019 |

OTHER PUBLICATIONS

Phillips et al. Rate of Asparagine Deamidation in a Monoclonal AntibodyCorrelating with Hydrogen Exchange Rate at Adjacent DownstreamResidues. Anal. Chem . Jan. 2017, 89, 2361-2368. (Year: 2017).*

International Search Report in International Application No. PCT/US2019/025363 mailed on Aug. 16, 2019.

Abdiche et al., Determining Kinetics and Affinities of Protein Interactions Using a Parallel Real-Time Label-Free Biosensor, the Octet, Analytical Biochemistry, Jun. 15, 2008, vol. 377, No. 2, pp. 209-217.

Brodeur et al., Monoclonal Antibody Production Techniques and Applications, vol. 33, 1987, pp. 51-63.

Bruggermann et al., Designer Mice: The Production of Human Antibody Repertoires in Transgenic Animals, Year in Immunol., vol. 7, 1993, pp. 33-40.

Chelius et al., Identification and Characterization Sites in the Conserved Regions of Human Immunoglobulin Gamma Antibodies, Anal. Chem.,vol. 77, Sep. 15, 2005, pp. 6004-6011.

(Continued)

*Primary Examiner* — Maher M Haddad
(74) *Attorney, Agent, or Firm* — Greenberg Traurig LLP

(57) ABSTRACT

The present disclosure generally relates to compositions and methods for treating a disease or condition associated with insufficient opening of Cx43 hemichannels in osteocytes, preferably for treating cancer, cancer metastasis, osteosarcoma, osteoporosis, or osteopenia.

11 Claims, 3 Drawing Sheets
Specification includes a Sequence Listing.

(56) References Cited

OTHER PUBLICATIONS

Chothia et al., Canonical Structures for the Hypervariable Regions of Immunoglobulins, J Mol. Biol. vol. 196, Aug. 20, 1987, pp. 901-917.

Chothia et al., Conformations of Immunoglobulin Hypervariable Regions, Nature, vol. 342, Dec. 1989, pp. 877-883.

Ehring, Hydrogen Exchange/Electrospray Ionization Mass Spectrometry Studies of Structural Features of Proteins and Protein/Protein Interactions, Analytical Biochemistry, vol. 267, Feb. 15, 1999, pp. 252-259.

Engen et al., Peer Reviewed: Investigating Protein Structure and Dynamics by Hydrogen Exchange MS, Analytical Chemistry, vol. 73, No. 9, May 1, 2001, pp. 257A-265A.

Fedchenko et al., Different Approaches for Interpretation and Reporting of Immunohistochemistry Analysis Results In the Bone Tissue—A Review, Diagnostic Pathology, vol. 9, No. 1, Dec. 2014, pp. 1-12.

Goeddel (ed.), Methods in Enzymology, vol. 185, Gene Expression Technology, Academic Press. N.Y. 1990, 681 pages (Book).

Harlow et al., Antibodies—A. Laboratory Manual, Cold Spring Harbor Laboratory Press, Cold Spring Harbor, New York (1988). (Book).

Hochleitner et al., Characterization of a Discontinuous Epitope of the Human Immunodeficiency Virus (HIV) Core Protein p24 by Epitope Excision and Differential Chemical Modification Followed by Mass Spectrometric Peptide Mapping Analysis, Protein Science, vol. 9, No. 3, Mar. 2000, pp. 487-496.

Hoogenboom et al., Human Antibodies from Synthetic Repertoires of Germline VH Gene Segments Rearranged in Vitro, J Mol. Biol. vol. 227, No. 2, Sep. 1992, pp. 381-388.

Jakobovits et al., Germ-Line Transmission and Expression of a Human-Derived Yeast Artificial Chromosome, Nature, vol. 362, Mar. 18, 1993, pp. 255-258.

Jakobovits et al., Analysis of Homozygous Mutant Chimeric Mice: Deletion of the Immunoglobulin Heavy-Chain Joining Region Blocks B-Cell Development and Antibody Production, Proc. Natl. Acad. Sci. USA, vol. 90, Mar. 1993, pp. 2551-2555.

Jones et al., Replacing the Complementarity-Determining Regions in a Human Antibody with Those from a Mouse, Nature, vol. 321, May 29, 1986, pp. 522-525.

Junghans et al., Anti-Tac-H, a Humanized Antibody to the Interleukin 2 Receptor with New Features for Immunotherapy in Malignant and Immune Disorders, Cancer Research, vol. 50, Mar. 1, 1990, pp. 1495-1502.

Kabat et al. Sequences of Proteins of Immunological Interest, vol. 1, 5th edition. Public Health Service, NIH, Bethesda, MD, 1991. (Book).

Kohler et al., Continuous Cultures of Fused Cells Secreting Antibody of Predefined Specificity, Nature, vol. 256, Aug. 7, 1975, pp. 495-497.

Kozbor et al., A Human Hybrid Myeloma for Production of Human Monoclonal Antibodies, J Immunol., vol. 133, No. 6, Dec. 1, 1984, pp. 3001-3005.

Manning et al., Stability of Protein Pharmaceuticals: An Update, Pharmaceutical Research, vol. 27 Issue 4, Apr. 2010, pp. 544-575.

Marks et al., By-Passing Immunization Human Antibodies from V-Gene Libraries Displayed on Phage, J Mol. Biol., vol. 222, Dec. 5, 1991, pp. 581-597.

McGill et al., Variations of Box Plots, The American Statistician, vol. 32, No. 1, 1978, pp. 12-16.

Morrison et al., Chimeric Human Antibody Molecules: Mouse Antigen-Binding Domains with Human Constant Region Domains, Proc. Natl. Acad. Sci. USA, vol. 81, Nov. 1984, pp. 6851-6855.

Musil et al., "Multisubunit Assembly of an Integral Plasma Membrane Channel Protein, Gap Junction Connexin43, Occurs After Exit from the ER", Cell, vol. 74, No. 6, Sep. 24, 1993, pp. 1065-1077.

Posthumus et al., Analysis and Simulation of a Neutraslizing Epitope of Transmissible Gastroenteritis Virus, Journal of Virology, vol. 64, No. 7, Jul. 1990, pp. 3304-3309.

Ramos-Vara et al., When Tissue Antigens and Antibodies Get Along: Revisiting the Technical Aspects of Immunohistochemistry—The Red, Brown, and Blue Technique, Veterinary Pathology, vol. 51, No. 1, Jan. 2014, pp. 42-87.

Reineke et al., Antibody Epitope Mapping Using Arrays of Synthetic Peptides, Antibody Engineering, vol. 248, 2004, pp. 443-463.

Riechmann et al., Reshaping Human Antibodies for Therapy, Nature, vol. 332, Mar. 24, 1988, pp. 323-327.

Sambrook et al., 2001, Molecular Cloning: A Laboratory Manual, 3rd ed., Cold Spring Harbor Laboratory Press, Cold Spring Harbor, New York. (Book).

Sela-Culang, et al., The Structural Basis of Antibody-Antigen Recognition, Frontiers in Immunology, vol. 4, Oct. 8, 2013, p. 302.

Strohl et al., Development Issues: Antibody Stability, Developability, Immunogenicity, and Comparability, Therapeutic Antibody Engineering: Current and Future Advances Driving the Strongest Growth Area in the Pharma Industry, 2012, pp. 377-403.

Verhoeyen et al., Reshaping Human Antibodies; Grafting an Antilysozyme Activity, Science 239, No. 4847, Mar. 25, 1988, pp. 534-1536.

Vincke et al., General Strategy to Humanize a Camelid Single-Domain Antibody and Identification of a Universal Humanized Nanobody Scaffold, J. Biol. Chem., vol. 284, No. 5, Jan. 30, 2009. pp. 3273-3284.

Bosch et al., "Hemichannels in Neurodegenerative Diseases: Is There a Link to Pathology?", Front. Cell. Neurosci., vol. 8, p. 242, 2014.

Gupta et al., "Oxidation and Deamidation of Monoclonal Antibody Products: Potential Impact on Stability, Biological Activity, and Efficacy", Journal of Pharmaceutical Sciences, vol. 111, pp. 903-918, 2022.

Li et al., "Connexin 43 Hemichannel as a Novel Mediator of Sterile and Infectious Inflammatory Diseases", Scientific Reports, vol. 8, p. 166, 2018.

Orellana et al., "Role of Connexin Hemichannels in Neurodegeneration", Neurodegenerative Diseases—Processes, Prevention, Protection and Monitoring, IntechOpen, London, UK, pp. 235-254, 2011.

Phillips et al., "Rate of Asparagine Deamidation in a Monoclonal Antibody Correlating with Hydrogen Exchange Rate at Adjacent Downstream Residues", Anal. Chem., vol. 89, pp. 2361-2368, 2017.

Sharif-Alhoseini et al., Animal Models of Spinal Cord Injury: A Systematic Review, Spinal Cord, vol. 55, pp. 714-721, 2017.

Vicario et al., "Connexins in the Central Nervous System: Physiological Traits and Neuroprotective Targets", Front. Physiol., vol. 8, p. 1060, 2017.

Webb, "Animal Models of Human Disease: Inflammation", Biochem. Pharmacol., vol. 87, pp. 121-130, 2014.

\* cited by examiner

SEQUENCE LISTING

```
<160> NUMBER OF SEQ ID NOS: 39

<210> SEQ ID NO 1
<211> LENGTH: 8
<212> TYPE: PRT
<213> ORGANISM: Unknown
<220> FEATURE:
<223> OTHER INFORMATION: Synthetic

<400> SEQUENCE: 1

Gly Tyr Thr Phe Thr Ser Tyr Tyr
1               5

<210> SEQ ID NO 2
<211> LENGTH: 8
<212> TYPE: PRT
<213> ORGANISM: Unknown
<220> FEATURE:
<223> OTHER INFORMATION: Synthetic

<400> SEQUENCE: 2

Ile Asn Pro Ser Asn Ala Gly Thr
1               5

<210> SEQ ID NO 3
<211> LENGTH: 12
<212> TYPE: PRT
<213> ORGANISM: Unknown
<220> FEATURE:
<223> OTHER INFORMATION: Synthetic
```

```
<400> SEQUENCE: 3

Thr Arg Glu Gly Asn Pro Tyr Tyr Thr Met Asn Tyr
1               5                   10

<210> SEQ ID NO 4
<211> LENGTH: 11
<212> TYPE: PRT
<213> ORGANISM: Unknown
<220> FEATURE:
<223> OTHER INFORMATION: Synthetic

<400> SEQUENCE: 4

Gln Ser Leu Leu Glu Ser Asp Gly Lys Thr Tyr
1               5                   10

<210> SEQ ID NO 5
<211> LENGTH: 3
<212> TYPE: PRT
<213> ORGANISM: Unknown
<220> FEATURE:
<223> OTHER INFORMATION: Synthetic

<400> SEQUENCE: 5

Leu Val Ser
1

<210> SEQ ID NO 6
<211> LENGTH: 9
<212> TYPE: PRT
<213> ORGANISM: Unknown
<220> FEATURE:
<223> OTHER INFORMATION: Synthetic

<400> SEQUENCE: 6

Trp Gln Gly Thr His Phe Pro Trp Thr
1               5

<210> SEQ ID NO 7
<211> LENGTH: 119
<212> TYPE: PRT
<213> ORGANISM: Unknown
<220> FEATURE:
<223> OTHER INFORMATION: Synthetic

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Ala Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser
        115
```

```
<210> SEQ ID NO 8
<211> LENGTH: 112
<212> TYPE: PRT
<213> ORGANISM: Unknown
<220> FEATURE:
<223> OTHER INFORMATION: Synthetic

<400> SEQUENCE: 8

Asp Val Val Met Thr Gln Ser Pro Leu Ser Leu Pro Val Thr Ile Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gly Gly Thr Lys Val Glu Ile Lys
            100                 105                 110

<210> SEQ ID NO 9
<211> LENGTH: 449
<212> TYPE: PRT
<213> ORGANISM: Unknown
<220> FEATURE:
<223> OTHER INFORMATION: Synthetic

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

-continued

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 10
<211> LENGTH: 446
<212> TYPE: PRT
<213> ORGANISM: Unknown
<220> FEATURE:
<223> OTHER INFORMATION: Synthetic

<400> SEQUENCE: 10

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
```

```
            115                 120                 125
Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 11
<211> LENGTH: 446
<212> TYPE: PRT
<213> ORGANISM: Unknown
<220> FEATURE:
<223> OTHER INFORMATION: Synthetic

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
```

```
                  35                  40                  45
Gly Gly Ile Asn Pro Ser Asn Ala Gly Thr Asn Phe Asn Glu Lys Phe
 50                  55                  60

Lys Asn Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Glu Gly Asn Pro Tyr Tyr Thr Met Asn Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
                195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
                435                 440                 445

<210> SEQ ID NO 12
```

```
<211> LENGTH: 449
<212> TYPE: PRT
<213> ORGANISM: Unknown
<220> FEATURE:
<223> OTHER INFORMATION: Synthetic

<400> SEQUENCE: 12
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

```
Ser Asn Gly Gln Pro Glu Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 13
<211> LENGTH: 449
<212> TYPE: PRT
<213> ORGANISM: Unknown
<220> FEATURE:
<223> OTHER INFORMATION: Synthetic

<400> SEQUENCE: 13

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
            35                  40                  45

Gly Gly Ile Asn Pro Ser Asn Ala Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 14
<211> LENGTH: 446
<212> TYPE: PRT
<213> ORGANISM: Unknown
<220> FEATURE:
<223> OTHER INFORMATION: Synthetic

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
```

```
            195                 200                 205
Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
                435                 440                 445

<210> SEQ ID NO 15
<211> LENGTH: 446
<212> TYPE: PRT
<213> ORGANISM: Unknown
<220> FEATURE:
<223> OTHER INFORMATION: Synthetic

<400> SEQUENCE: 15

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Gly Ile Asn Pro Ser Asn Ala Gly Thr Asn Phe Asn Glu Lys Phe
        50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
                100                 105                 110

Thr Leu Val Thr Val Ser Ser Ala Ser Thr Lys Gly Pro Ser Val Phe
```

```
            115                 120                 125
Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 16
<211> LENGTH: 446
<212> TYPE: PRT
<213> ORGANISM: Unknown
<220> FEATURE:
<223> OTHER INFORMATION: Synthetic

<400> SEQUENCE: 16

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
```

```
             35                  40                  45
Gly Gly Ile Asn Pro Ser Asn Gly Gly Thr Asn Phe Asn Glu Lys Phe
 50                  55                  60

Lys Asn Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Glu Gly Asn Pro Tyr Tyr Thr Met Asn Tyr Trp Gly Gln Gly
                100                 105                 110

Thr Leu Val Thr Val Ser Ser Ala Ser Thr Lys Gly Pro Ser Val Phe
             115                 120                 125

Pro Leu Ala Pro Cys Ser Arg Ser Thr Ser Glu Ser Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 17
```

<211> LENGTH: 446
<212> TYPE: PRT
<213> ORGANISM: Unknown
<220> FEATURE:
<223> OTHER INFORMATION: Synthetic

<400> SEQUENCE: 17

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met Tyr Trp Val Arg Gln Ala Pro Gly Gln Gly Leu Glu Trp Ile
        35                  40                  45
Gly Gly Ile Asn Pro Ser Asn Ala Gly Thr Asn Phe Asn Glu Lys Phe
    50                  55                  60
Lys Asn Arg Ala Thr Leu Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Thr Arg Glu Gly Asn Pro Tyr Tyr Thr Met Asn Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
    210                 215                 220
Cys Pro Pro Cys Pro Ala Pro Glu Ala Ala Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
```

```
Gln Pro Glu Asn Asn Tyr Lys Thr Thr Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Asn His Tyr Thr Gln Lys Ser Leu Ser Leu Ser Leu Gly Lys
        435                 440                 445

<210> SEQ ID NO 18
<211> LENGTH: 219
<212> TYPE: PRT
<213> ORGANISM: Unknown
<220> FEATURE:
<223> OTHER INFORMATION: Synthetic

<400> SEQUENCE: 18

Asp Val Val Met Thr Gln Ser Pro Leu Ser Leu Pro Val Thr Ile Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 19
<211> LENGTH: 10
<212> TYPE: PRT
<213> ORGANISM: Homo sapiens

<400> SEQUENCE: 19

Phe Leu Ser Arg Pro Thr Glu Lys Thr Ile
1               5                   10

<210> SEQ ID NO 20
<211> LENGTH: 10
```

<212> TYPE: PRT
<213> ORGANISM: Unknown
<220> FEATURE:
<223> OTHER INFORMATION: Synthetic

<400> SEQUENCE: 20

Phe Trp Ser Arg Pro Thr Glu Lys Thr Ile
1               5                   10

<210> SEQ ID NO 21
<211> LENGTH: 10
<212> TYPE: PRT
<213> ORGANISM: Unknown
<220> FEATURE:
<223> OTHER INFORMATION: Synthetic

<400> SEQUENCE: 21

Phe Leu Ser Arg Pro Thr Glu Lys Thr Cys
1               5                   10

<210> SEQ ID NO 22
<211> LENGTH: 10
<212> TYPE: PRT
<213> ORGANISM: Unknown
<220> FEATURE:
<223> OTHER INFORMATION: Synthetic

<400> SEQUENCE: 22

Phe Leu Gly Arg Pro Thr Glu Lys Thr Ile
1               5                   10

<210> SEQ ID NO 23
<211> LENGTH: 10
<212> TYPE: PRT
<213> ORGANISM: Unknown
<220> FEATURE:
<223> OTHER INFORMATION: Synthetic

<400> SEQUENCE: 23

Phe Leu Ser Arg Pro Thr Glu Lys Asp Ile
1               5                   10

<210> SEQ ID NO 24
<211> LENGTH: 10
<212> TYPE: PRT
<213> ORGANISM: Unknown
<220> FEATURE:
<223> OTHER INFORMATION: Synthetic

<400> SEQUENCE: 24

Phe Leu Ser Arg Pro Thr Glu Lys Tyr Ile
1               5                   10

<210> SEQ ID NO 25
<211> LENGTH: 10
<212> TYPE: PRT
<213> ORGANISM: Unknown
<220> FEATURE:
<223> OTHER INFORMATION: Synthetic

<400> SEQUENCE: 25

Phe Leu Ser Arg Trp Thr Glu Lys Thr Ile
1               5                   10

<210> SEQ ID NO 26
<211> LENGTH: 10
<212> TYPE: PRT

```
<213> ORGANISM: Unknown
<220> FEATURE:
<223> OTHER INFORMATION: Synthetic

<400> SEQUENCE: 26

Phe Leu Ser Arg Pro Ser Glu Lys Thr Ile
1               5                   10

<210> SEQ ID NO 27
<211> LENGTH: 10
<212> TYPE: PRT
<213> ORGANISM: Unknown
<220> FEATURE:
<223> OTHER INFORMATION: Synthetic

<400> SEQUENCE: 27

Phe Leu Asn Arg Pro Thr Glu Lys Thr Ile
1               5                   10

<210> SEQ ID NO 28
<211> LENGTH: 10
<212> TYPE: PRT
<213> ORGANISM: Unknown
<220> FEATURE:
<223> OTHER INFORMATION: Synthetic

<400> SEQUENCE: 28

Phe Leu Ser Arg Pro Phe Glu Lys Thr Ile
1               5                   10

<210> SEQ ID NO 29
<211> LENGTH: 10
<212> TYPE: PRT
<213> ORGANISM: Unknown
<220> FEATURE:
<223> OTHER INFORMATION: Sythetic

<400> SEQUENCE: 29

Phe Leu Ser Arg Pro Thr Glu Lys Thr Gly
1               5                   10

<210> SEQ ID NO 30
<211> LENGTH: 5
<212> TYPE: PRT
<213> ORGANISM: Unknown
<220> FEATURE:
<223> OTHER INFORMATION: Synthetic

<400> SEQUENCE: 30

Phe Leu Ser Arg Pro
1               5

<210> SEQ ID NO 31
<211> LENGTH: 5
<212> TYPE: PRT
<213> ORGANISM: Unknown
<220> FEATURE:
<223> OTHER INFORMATION: Synthetic

<400> SEQUENCE: 31

Leu Ser Arg Pro Thr
1               5

<210> SEQ ID NO 32
<211> LENGTH: 5
<212> TYPE: PRT
<213> ORGANISM: Unknown
```

```
<220> FEATURE:
<223> OTHER INFORMATION: Synthetic

<400> SEQUENCE: 32

Ser Arg Pro Thr Glu
1               5

<210> SEQ ID NO 33
<211> LENGTH: 5
<212> TYPE: PRT
<213> ORGANISM: Unknown
<220> FEATURE:
<223> OTHER INFORMATION: Synthetic

<400> SEQUENCE: 33

Arg Pro Thr Glu Lys
1               5

<210> SEQ ID NO 34
<211> LENGTH: 5
<212> TYPE: PRT
<213> ORGANISM: Unknown
<220> FEATURE:
<223> OTHER INFORMATION: Synthetic

<400> SEQUENCE: 34

Pro Thr Glu Lys Thr
1               5

<210> SEQ ID NO 35
<211> LENGTH: 5
<212> TYPE: PRT
<213> ORGANISM: Unknown
<220> FEATURE:
<223> OTHER INFORMATION: Synthetic

<400> SEQUENCE: 35

Thr Glu Lys Thr Ile
1               5

<210> SEQ ID NO 36
<211> LENGTH: 6
<212> TYPE: PRT
<213> ORGANISM: Unknown
<220> FEATURE:
<223> OTHER INFORMATION: Synthetic

<400> SEQUENCE: 36

Phe Leu Ser Arg Pro Thr
1               5

<210> SEQ ID NO 37
<211> LENGTH: 6
<212> TYPE: PRT
<213> ORGANISM: Unknown
<220> FEATURE:
<223> OTHER INFORMATION: Synthetic

<400> SEQUENCE: 37

Leu Ser Arg Pro Thr Glu
1               5

<210> SEQ ID NO 38
<211> LENGTH: 6
<212> TYPE: PRT
<213> ORGANISM: Unknown
<220> FEATURE:
```

```
<223> OTHER INFORMATION: Synthetic

<400> SEQUENCE: 38

Ser Arg Pro Thr Glu Lys
1               5

<210> SEQ ID NO 39
<211> LENGTH: 6
<212> TYPE: PRT
<213> ORGANISM: Unknown
<220> FEATURE:
<223> OTHER INFORMATION: Synthetic

<400> SEQUENCE: 39

Arg Pro Thr Glu Lys Thr
1               5
```

CONNEXIN 43 ANTIBODIES AND USE THEREOF

CROSS-REFERENCE TO RELATED APPLICATIONS

This application claims priority to and the benefit of U.S. Provisional Patent Application No. 62/651,668 filed Apr. 2, 2018, incorporated herein by reference in its entirety.

SEQUENCE LISTING

The ASCII text file submitted herewith via EFS-Web, entitled "172628_020301_sequence.txt" created on Apr. 1, 2019, having a size of 43.787 bytes, is hereby incorporated by reference in its entirety.

FIELD

The present disclosure generally relates to anti-connexin (Cx) 43 antibodies and their use in the treatment of, e.g., a disease or condition associated with opening of Cx43 hemichannels in osteocytes.

BACKGROUND

Despite multiple preventative and therapeutic approaches, cancer is one of the major causes of death worldwide. Between 2010 and 2020, the number of new cancer cases in the United States is expected to increase by about 24% in men to more than 1 million cases per year, and by about 21% in women to more than 900,000 cases per year. The types of cancer that are expected to increase the most are melanoma in both men and women; prostate, kidney, liver, and bladder cancers in men; and lung, breast, uterine, and thyroid cancers in women. Cancer remains the second most common cause of death in the US, accounting for nearly 1 of every 4 deaths. Many cancers are difficult or impossible to treat with current approaches. Many cancers evade current treatment regimens, become resistant to treatment, or reoccur after treatment.

Cancer metastasis occurs when a cancer spreads from the part of the body where it originated (e.g., breast or prostate) to other parts of the body (e.g., liver or bone) and establishes a secondary tumor. The bone is one of the most common sites of cancer metastasis. Cancers that metastasize to bone include, but are not limited to breast cancer, prostate cancer, lung cancer, and skin cancers (e.g., melanoma). Bone metastasis can be identified in up to 75% of patients with advanced breast and prostate cancers. Bone metastasis (mets) are associated with many significant clinical and quality of life consequences, such as, but not limited to intractable pain, pathological fractures, spinal cord and nerve compression, bone marrow infiltration, and impaired motility. In many cases the systemic presence of a cancer can also make the cancer incurable.

Normal bone is made up of three major cell types: bone-forming osteoblasts, bone-resorbing osteoclasts, and osteocytes. Osteocytes make up approximately 95% of bone cells and maintain the bone remodeling process by coordinating osteolytic and osteoblastic activities. When cancer cells invade the bone, many of the normal bone functions are affected. Cancer cells interact with the local microenvironment to promote cancer cell survival via bone destruction and vascularization.

Osteocytes express hemichannels known as connexin (Cx) 43 hemichannels. These osteocyte hemichannels are normally closed and can be opened when exposed to mechano-stimulation, which leads to the release of various factors into the bone microenvironment. The factors released by hemichannel opening can mediate other processes that can decrease tumor cell migration and bone metastasis. Alendronate (AD), an efficacious and commonly used bisphosphonate drug has been shown to be able to open Cx43 hemichannels in osteocytes. Bisphosphonates are a class of drugs known for treating many bone disorders including bone metastasis. It has been shown that administration of bisphosphonates to be associated with a decrease in the incidence of bone metastasis and a decrease in death rate in patients with breast cancer. AD has been associated with decreased tumor growth as well as reduced bone destruction and pain. AD inhibits osteoclast activity and induces the opening of Cx43 hemichannels in osteocytes. However, AD administration is accompanied by multiple, severe side-effects.

As such, a need exists for effective methods and compositions to treat cancer metastasis, such as by opening Cx43 hemichannels.

SUMMARY

Provided herein are compositions and methods for treating a disease or condition associated with opening (e.g., insufficient or defective opening) of Cx43 hemichannels in osteocytes, such as cancer, cancer metastasis, osteosarcoma, osteoporosis, or osteopenia.

In one aspect, provided herein is an anti-Cx43 antibody, or antigen binding fragment thereof, comprising:
  a first, second and third heavy chain complementarity determining region (CDR) sequence having the amino acid sequence of SEQ ID NOs: 1, 2, and 3, respectively; and
  a first, second and third light chain CDR sequence having the amino acid sequence of SEQ ID NOs: 4, 5, and 6, respectively.

In some embodiments, the antibody or fragment thereof can have a heavy chain variable domain having the amino acid sequence of SEQ ID NO: 7, and a light chain variable domain having the amino acid sequence of SEQ ID NO: 8.

In another aspect, provided herein is an anti-Cx43 antibody, or antigen binding fragment thereof, comprising a heavy chain having an amino acid sequence selected from the group consisting of SEQ ID NOs: 9-17, and a light chain having the amino acid sequence of SEQ ID NO: 18.

In another aspect, provided herein is an antibody that binds an epitope located within the amino add sequence of FLSRPTEKTI (SEQ ID NO: 19). In some embodiments, the epitope can comprise one or more amino acids selected from the group consisting of F1, S3, R4, P5, T6, E7, K8, T9 and I10 of SEQ ID NO: 19. In one embodiment, the epitope consists of F1, S3, R4, P5, T6, E7, K8, T9 and I10 of SEQ ID NO: 19. In some embodiments, tire epitope can include all ten amino acids of SEQ ID NO: 19. In certain embodiments, the epitope consists of all ten amino acids of SEQ ID NO. 19.

In a further aspect, provided herein is an isolated anti-Cx43 antibody, or antigen binding fragment thereof, wherein the antibody or fragment thereof cross-competes for binding to Cx43 with any antibody or fragment thereof disclosed herein. In certain embodiments, the antibody or fragment thereof promotes opening of Cx43 hemichannels in osteocytes.

In another aspect, provided herein is a pharmaceutical composition for promoting opening of Cx43 hemichannels in osteocytes, preferably for treating cancer, cancer metastasis, osteosarcoma, osteoporosis, or osteopenia, comprising the antibody or fragment thereof disclosed herein and a pharmaceutically acceptable carrier.

Also provided herein is use of the antibody or fragment thereof disclosed herein for the manufacture of a medicament for promoting opening of Cx43 hemichannels in osteocytes, preferably for treating cancer, cancer metastasis, osteoporosis, or osteopenia.

Additionally provided herein is a method of promoting opening of Cx43 hemichannels in osteocytes, preferably for treating cancer, cancer metastasis, osteosarcoma, osteoporosis, or osteopenia, comprising contacting the osteocytes with an effective amount of the antibody or fragment thereof disclosed herein.

Also provided herein is a method for treating a disease or condition associated with opening (e.g., insufficient opening) of Cx43 hemichannels in osteocytes, preferably for treating cancer, cancer metastasis, osteosarcoma, osteoporosis, or osteopenia, comprising administering a therapeutically effective amount of the antibody or fragment thereof disclosed herein to a patient in need thereof.

DETAILED DESCRIPTION

Figure 1:
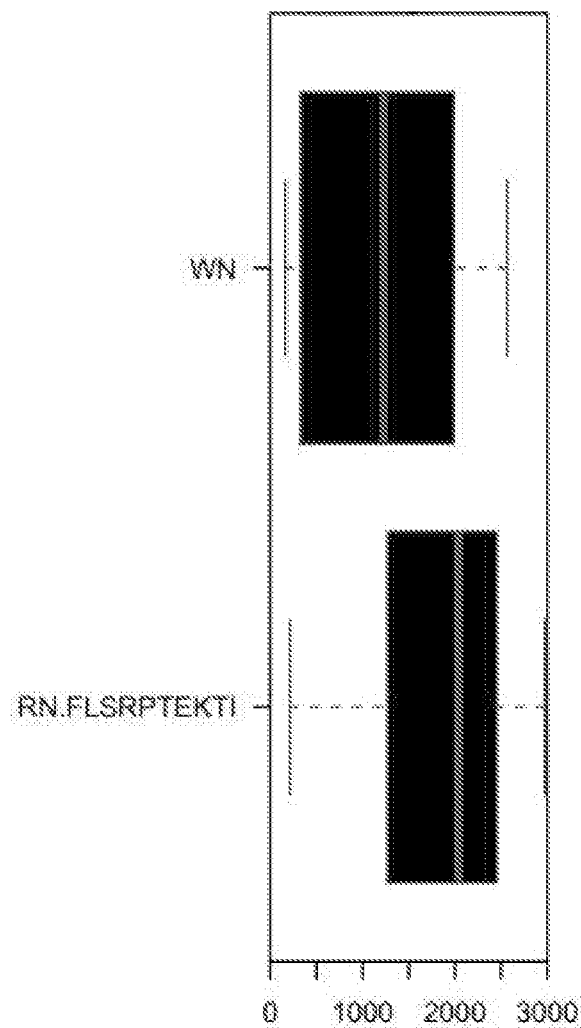
FIG. 1. Box plot graphs of raw data of antibody screening.

It is to be understood that both the foregoing general description and the following detailed description are exemplary and explanatory only and are not restrictive of the compositions and methods of the present disclosure.

Disclosed herein are compositions and methods related to anti-Cx43 antibodies, or antigen-binding fragment thereof. In some embodiments, the compositions disclosed herein display superior activity, drugability (e.g., reduced toxicity), stability and/or developability (e.g., reduced cost of production) over those disclosed in PCT Publication Nos. WO 2015/027120 and WO 2017/147561, both of which are incorporated herein by reference in their entirety. In certain embodiments, the advantages are unexpected.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

As used herein, the following terms and phrases are intended to have the following meanings:

The articles "a" and "an" are used herein to refer to one or to more than one (i.e., to at least one) of the grammatical object of the article. By way of example, "an element" means one element or more than one element.

As used herein, the term "about" means acceptable variations within 20%, more preferably within 10% and most preferably within 5% of the stated value.

An "anti-Cx43 antibody" is an antibody that immunospecifically binds to Cx43 (e.g., its extracellular domain). The antibody may be an isolated antibody. Such binding to Cx43 exhibits a $K_D$ with a value of, e.g., no greater than 1 µM, no greater than 100 nM or no greater than 50 nM. $K_D$ can be measured by any methods known to one skilled in the art, such as a surface plasmon resonance assay or a cell binding assay. An anti-Cx43 antibody may be a monoclonal antibody, or antigen-binding fragments thereof.

An "antibody," as used herein is a protein comprising binding domains that bind to a target epitope. The term antibody includes monoclonal antibodies comprising immunoglobulin heavy and light chain molecules, single heavy chain variable domain antibodies, and variants and derivatives thereof, including chimeric variants of monoclonal and single heavy chain variable domain antibodies. Binding domains are substantially encoded by immunoglobulin genes or fragments of immunoglobulin genes, wherein the protein immunospecifically binds to an antigen. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. For most vertebrate organisms, including humans and murine species, the typical immunoglobulin structural unit comprises a tetramer that is composed of two identical pairs of polypeptide chains, each pair having one "light" (about 25 kD) and one "heavy" chain (about 50-70 kD). "$V_L$" and $V_H$" refer to the variable domains of these light and heavy chains respectively. "$C_L$" and $C_H$" refer to the constant domains of the light and heavy chains. Loops of β-strands, three each on the $V_L$ and $V_H$ are responsible for binding to the antigen, and are referred to as the "complementarity determining regions" or "CDRs". The "Fab" (fragment, antigen-binding) region includes one constant and one variable domain from each heavy and light chain of the antibody, i.e., $V_L$, $C_L$, $V_H$ and $C_H1$.

Antibodies include intact immunoglobulins as well as antigen-binding fragments thereof. The term "antigen-binding fragment" refers to a polypeptide fragment of an antibody which binds antigen or competes with intact antibody (i.e., with the intact antibody from which they were derived) for antigen binding (i.e., specific binding). Antigen binding fragments can be produced by recombinant or biochemical methods that are well known in the art. Exemplary antigen-binding fragments include Fv, Fab, Fab', $(Fab')_2$, CDR, paratope and single chain Fv antibodies (scFv) in which a $V_H$ and a $V_L$ chain are joined together (directly or through a peptide linker) to form a continuous polypeptide.

Antibodies also include variants, chimeric antibodies and humanized antibodies. The term "antibody variant" as used herein refers to an antibody with single or multiple mutations in the heavy chains and/or light chains. In some embodiments, the mutations exist in the variable region. In some embodiments, the mutations exist in the constant region. "Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non-human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example. "Humanized" antibodies refer to a molecule having an antigen-binding site that is substantially derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, or six) which are altered with respect to the original antibody, which are also termed one or more CDRs "derived from" one or more CDRs.

As described herein, the amino acid residues of an antibody can be numbered according to the general numbering of Kabat (Kabat, et al. (1991) Sequences of Proteins of Immunological Interest, 5th edition. Public Health Service, N1H, Bethesda, MD).

The term "binding" as used herein in the context of binding between an antibody and an epitope of Cx43 as a target, refers to the process of a non-covalent interaction between molecules. Preferably, said binding is specific. The specificity of an antibody can be determined based on affinity. A specific antibody can have a binding affinity or dissociation constant $K_D$ for its epitope of less than $10^{-7}$ M, preferably less than $10^{-8}$ M.

The term "affinity" refers to the strength of a binding reaction between a binding domain of an antibody and an epitope. It is the sum of the attractive and repulsive forces operating between the binding domain and the epitope. The term affinity, as used herein, refers to the dissociation constant, $K_D$.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "cancer" broadly refers to an uncontrolled, abnormal growth of a host's own cells leading to invasion of surrounding tissue and potentially tissue distal to the initial site of abnormal cell growth in the host. Major classes include carcinomas which are cancers of the epithelial tissue (e.g., skin, squamous cells); sarcomas which are cancers of the connective tissue (e.g., bone, cartilage, fat, muscle, blood vessels, etc.); leukemias which are cancers of blood forming tissue (e.g., bone marrow tissue); lymphomas and myelomas which are cancers of immune cells; and central nervous system cancers which include cancers from brain and spinal tissue. "Cancer(s)," "neoplasm(s)," and "tumor(s)" are used herein interchangeably. As used herein, "cancer" refers to all types of cancer or neoplasm or malignant tumors including leukemias, carcinomas and sarcomas, whether new or recurring. Specific examples of cancers are: carcinomas, sarcomas, myelomas, leukemias, lymphomas and mixed type tumors. Non-limiting examples of cancers are new or recurring cancers of the brain, melanoma, bladder, breast, cervix, colon, head and neck, kidney, lung, non-small cell lung, mesothelioma, ovary, prostate, sarcoma, stomach, uterus and medulloblastoma.

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. In one embodiment, an epitope is a region of an antigen that is bound by an antibody. In certain embodiments, an antibody is said to specifically bind an antigen when it preferentially recognizes its target antigen in a complex mixture of proteins and/or macromolecules. Methods for epitope mapping are well known in the art, such as X-ray co-crystallography, array-based oligo-peptide scanning, site-directed mutagenesis, high throughput mutagenesis mapping and hydrogen-deuterium exchange. Epitopes can be formed both from contiguous amino acids or noncontiguous amino acids juxtaposed by tertiary folding of a protein. Epitopes formed front contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

The site on the antibody that binds the epitope is referred to as "paratope," which typically include amino acid residues that are in close proximity to the epitope once bound. See Sela-Culang et al., Front Immunol. 2013; 4: 302.

"Immunohistochemistry" or "IHC" refers to the process of detecting an antigen in cells of a tissue section allowing the binding and subsequent detection of antibodies immunospecifically recognizing the antigen of interest in a biological tissue. For a review of the IHC technique, see, e.g., Ramos-Vara et al., Veterinary Pathology January 2014 vol. 51 no. 1, 42-87, incorporated herein by reference in its entirety. To evaluate IHC results, different qualitative and semi-quantitative scoring systems have been developed. See, e.g., Fedchenko et al., Diagnostic Pathology, 2014; 9: 221, incorporated herein by reference in its entirety. One example is the H-score, determined by adding the results of multiplication of the percentage of cells with staining intensity ordinal value (scored from 0 for "no signal" to 3 for "strong signal") with 300 possible values.

"Immunospecific" or "immunospecifically" (sometimes used interchangeably with "specifically") refer to antibodies that bind via domains substantially encoded by immunoglobulin genes or fragments of immunoglobulin genes to one or more epitopes of a protein of interest, but which do not substantially recognize and bind other molecules in a sample containing a mixed population of antigenic molecules. Typically, an antibody binds immunospecifically to a cognate antigen with a $K_D$ with a value of no greater than 50 nM, as measured by, e.g., real-lime, label free bio-layer interferometry assay, e.g., an Octet® HTX biosensor, or by surface plasmon resonance, e.g., BIACORE™, or by solution-affinity ELISA. The use of such assays is well known in the art.

The term "surface plasmon resonance", refers to an optical phenomenon that allows for the analysis of real-time biomolecular interactions by detection of alterations in protein concentrations within a biosensor matrix, for example using the BIACORE™ system (Pharmacia Biosensor AB, Uppsala. Sweden and Piscataway, N.J.)

Bio-layer interferometry is a label-free technology for measuring biomolecular interactions. It is an optical analytical technique that analyzes the interference pattern of white light reflected from two surfaces: a layer of immobilized protein on the biosensor tip, and an internal reference layer. Any change in the number of molecules bound to the biosensor tip causes a shift in the interference pattern that can be measured in real-time (Abdiche, Y. N., et al. Analytical Biochemistry, (2008), 377(2), 209-217). In certain embodiments, a "real-time bio-layer interferometer based biosensor (Octet HTX assay)" was used to assess the binding characteristics of certain anti-Cx43 antibodies disclosed herein.

The terms "cross-compete", "cross-competition", "cross-block", "cross-blocked" and "cross-blocking" are used interchangeably herein to mean the ability of an antibody or fragment thereof to interfere with the binding directly or indirectly through allosteric modulation of the anti-Cx43 antibodies of the present disclosure to the target Cx43. The extent to which an antibody or fragment thereof is able to interfere with the binding of another to the target, and therefore whether it can be said to cross-block or cross-compete according to the present disclosure, can be determined using competition binding assays. One particularly suitable quantitative cross-competition assay uses a FACS- or an AlphaScreen-based approach to measure competition between the labelled (e g. His tagged, biotinylated or radioactive labelled) an antibody or fragment thereof and the other an antibody or fragment thereof in terms of their binding to the target. In general, a cross-competing antibody or fragment thereof is for example one which can bind to the target in the cross-competition assay such that, during the assay and in the presence of a second antibody or fragment thereof, the recorded displacement of the immunoglobulin single variable domain or polypeptide according to the disclosure is up to 100% (e.g., in FACS based competition assay) of the maximum theoretical displacement (e.g., displacement by cold (e.g., unlabeled) antibody or fragment thereof that needs to be cross-blocked) by the to be tested potentially cross-blocking antibody or fragment thereof that is present in a given amount. Preferably, cross-competing antibodies or fragments thereof have a recorded displacement that is between 10% and 100%, more preferred between 50% to 100%.

Cross-competition between antibodies may also be measured by a real-time, label-free bio-layer interferometry assay. Cross-competition between two antibodies may be expressed as the binding of the second antibody that is less than the background signal due to self-self binding (wherein first and second antibodies is the same antibody). Cross-competition between 2 antibodies may be expressed, for example, as % binding of the second antibody that is less than the baseline self-self background binding (wherein first and second antibodies is the same antibody).

The terms "promote," "enhance" and "induce" as used interchangeably herein, refer to any statistically significant increase in biological activity (e.g., hemichannel opening). For example, "promotion" can refer to an increase of about 10%, 20%, 30%, 40%, 50%, 60%, 70%, 80%, 90%, or 100% in biological activity.

The term "subject" or "patient" includes a human or other mammalian animal that receives either prophylactic or therapeutic treatment.

The terms "treat," "treating," and "treatment," as used herein, refer to therapeutic or preventative measures such as those described herein. The methods of "treatment" employ administration to a patient a Cx43 ligand provided herein, for example, a patient having a cancer, in order to prevent, cure, delay, reduce the severity of, or ameliorate one or more symptoms of the cancer or recurring cancer, or in order to prolong the survival of a patient beyond that expected in the absence of such treatment. The methods of "treatment" also employ administration to a patient a Cx43 ligand provided herein (e.g., an antibody) to provide cancer therapy in a patient beyond that expected in the absence of such treatment.

The term "effective amount," as used herein, refers to that amount of an agent, such as a Cx43 ligand, for example an anti-Cx43 antibody, which is sufficient to effect treatment, prognosis or diagnosis of a cancer, when administered to a patient. A therapeutically effective amount will vary depending upon the patient and disease condition being treated, the weight and age of the patient, the severity of the disease condition, the manner of administration and tire like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of art antibody or antigen binding portion thereof, as provided herein. Dosing may be, e.g., every week, every 2 weeks, every three weeks, every 4 weeks, every 5 weeks or every 6 weeks. Dosage regimens may be adjusted to provide the optimum therapeutic response. An effective amount is also one in which any toxic or detrimental effects (side effects) of the agent are minimized and/or outweighed by the beneficial effects. Administration may be intravenous at exactly or about 6 mg/kg or 12 mg/kg weekly, or 12 mg/kg or 24 mg/kg biweekly. Additional dosing regimens are described below.

Other terms used in the fields of recombinant nucleic acid technology, microbiology, immunology, antibody engineering, and molecular and cell biology as used herein will be generally understood by one of ordinary skill in the applicable arts. For example, conventional techniques may be used for preparing recombinant DNA, performing oligonucleotide synthesis, and practicing tissue culture and transformation (e.g., electroporation, transfection or lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., Sambrook et al., 2001, *Molecular Cloning: A Laboratory Manual* 3rd ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Various aspects and embodiments are described in further detail in the following subsections.

Cx43

Various cells are able to communicate with each other and with the extracellular environment through hemichannels and gap junctions formed by the protein connexin. Connexin proteins are ubiquitously expressed throughout the body. Six connexin proteins make up one hemichannel, and 2 hemichannels make up 1 gap junction channel. Gap junctions are a cluster of channels that are located in the plasma membrane between adjoining cells and they mediate intercellular communication. Hemichannels are a separate entity from gap junction channels. Hemichannels permit the exchange of molecules between the intracellular compartments and the extracellular environment.

Osteocytes express hemichannels known as connexin (Cx) 43 hemichannels. These osteocyte hemichannels are normally closed and can be opened when exposed to mechano-stimulation, which leads to the release of various factors into the bone microenvironment. The factors released by hemichannel opening can mediate other processes that can decrease tumor cell migration and bone metastasis.

Connexin-43 is also known as gap junction alpha-1 protein (GJA1), which is a 43.0 kDa protein composed of 382 amino acids (NCBI Reference Sequence: NP_000156.1). GJA1 contains a long C-terminal tail, an N-terminal domain, and multiple transmembrane domains. The protein passes through the phospholipid bilayer four times, leaving its C- and N-terminals exposed to the cytoplasm. The C-terminal tail is composed of 50 amino acids and includes post-translational modification sites, as well as binding sites for transcription factors, cytoskeleton elements, and other proteins. As a result, the C-terminal tail is central to functions such as regulating pH gating and channel assembly. Notably, the DNA region of the GJA1 gene (NCBI Gene ID: 2697) encoding this tail is highly conserved, indicating that it is either resistant to mutations or becomes lethal when mutated. Meanwhile, the N-terminal domain is involved in channel gating and oligomerization and, thus, may control the switch between the channel's open and closed states. The transmembrane domains form the gap junction channel while the extracellular loops facilitate proper channel docking. Moreover, two extracellular loops form disulfide bonds that interact with two hexamers to form a complete gap junction channel.

Anti-Cx43 Antibody

Promoting or enhancing Cx43 hemichannel opening can induce or promote opening of Cx43 hemichannels in osteocytes, thereby treating, e.g., cancer, cancer metastasis, osteosarcoma, osteoporosis, or osteopenia. As such, anti-Cx43 antibodies can be used as an effective agent in cancer therapeutics.

In certain embodiments, the anti-Cx43 antibody can be a monoclonal antibody or an antigen-binding fragment thereof. In certain embodiments, the anti-Cx43 antibody can be a modified, e.g., chimeric or humanized antibody derived from a mouse anti-Cx43 antibody. In some embodiments, the anti-Cx43 antibody is an antibody or antigen binding fragment thereof which binds to an epitope present on the human Cx43 protein, e.g., the extracellular loops, or a portion thereof.

Exemplary anti-Cx43 antibodies can have one or more of the following CDR sequences:

```
Heavy chain:
CDR1 (SEQ ID NO.: 1):
GYTFTSYY

CDR2 (SEQ ID NO.: 2):
INPSNAGT

CDR3 (SEQ ID NO.: 3):
TREGNPYYTMNY

Light chain:
CDR1 (SEQ ID NO.: 4):
QSLLESDGKTY

CDR2 (SEQ ID NO.: 5):
LVS

CDR3 (SEQ ID NO.: 6):
WQGTHFPWT
```

In some embodiments, it has been surprisingly discovered that antibodies having the above CDR sequences show superior binding affinity and/or antibody stability, compared to those disclosed in PCT Publication Nos. WO 2015/027120 and WO 2017/147561. Without wishing to be bound by theory, it is believed that the "NG" to "NA" mutation in heavy chain CDR2 can reduce deamidation. Antibody deamidation especially in the CDR region may cause binding affinity change, antibody degradation, and charge variants changes, which can affect antibody function and increase the cost of antibody production. As such, the CDRs disclosed herein provide improved binding affinity and antibody stability, resulting in an advantageous technical effect over those disclosed in PCT Publication Nos. WO 2015/027120 and WO 2017/147561.

Monoclonal antibodies can be humanized and optimized using, e.g., CDR grafting, germline modeling and 3-D structure analysis, to increase the drugability and/or developabdity of the antibodies. In some embodiments, after humanization, the anti-Cx43 antibody can have one or both of the following variable domains:

```
Heavy Chain variable domain (SEQ ID NO.: 7):
EVQLVQSGAEVICKPGASVKVSCKASGYTFTSYYMYWVRQAPGQGLEWIG

GINPSNAGTNFNEKFKNRATLTVDKSTSTAYMELSSLRSEDTAVYYCTRE

GNPYYTMNYWGQGTLVTVSS

Light Chain variable domain (SEQ ID NO.: 8):
DVVMTQSPLSLPVTIGQPASISCKSSQSLLESDGKTYLNWLQQRPGQSPR

RLIYLVSKLDSGVPDRFSGSGSGTDFTLKISRVEAEDVGVYYCWQGTHFP

WTFGGGTKVEIK
```

In select embodiments, the anti-Cx43 antibody can have a variable domain fused to the constant regain of, e.g., human IgG1 or IgG4 that can optionally contain one or more mutations. In some embodiments, the mutations can be designed to reduce or minimize the cytotoxic effector function of the antibody, while maintaining binding affinity and antibody stability. For example, the anti-Cx43 antibody can have one or more of the following heavy chain sequences (wherein the bold portion corresponds to the variable domain and the non-bolded portion corresponds to the constant region):

```
>Heavy chain of Ab#D
                                      (SEQ ID NO.: 9)
EVQLVQSGAEVKKPGASVKVSCKASGYTFTSYYMYWVRQAPGQGLEWIGG INPSNgGTNFNEKFKNRATLTVDKSTSTAYMELSSLRSEDTAVYYCTREG

NPYYTMNYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVUTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

>Heavy chain of Ab#F
                                     (SEQ ID NO.: 10)
EVQLVQSGAEVKKPGASVKVSCKASGYTFTSYYMYWVRQAPGQGLEWIGG INPSNgGTNFNEKFKNRATLTVDKSTSTAYMELSSLRSEDTAVYYCTREG

NPYYTMNYWGQGTLVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFLGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK

>Heavy chain of Ab#H
                                     (SEQ ID NO.: 11)
EVQLVQSGAEVKKPGASVKVSCKASGYTFTSYYMYWVRQAPGQGLEWIGG INPSNaGTNFNEKFKNRATLTVDKSTSTAYMELSSLRSEDTAVYYCTREG

NPYYTMNYWGQGTLVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFLGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK

>Heavy chain of Ab#J
                                     (SEQ ID NO.: 12)
EVQLVQSGAEVKKPGASVKVSCKASGYTFTSYYMYWVRQAPGQGLEWIGG INPSNgGTNFNEKFKNRATLTVDKSTSTAYMELSSLRSEDTAVYYCTREG

NPYYTMNYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

>Heavy chain of Ab#L
                                     (SEQ ID NO.: 13)
EVQLVQSGAEVKKPGASVKVSCKASGYTFTSYYMYWVRQAPGQGLEWIGG INPSNaGTNFNEKFKNRATLTVDKSTSTAYMELSSLRSEDTAVYYCTREG

NPYYTMNYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTIPPVL

DSDGSFFLYSKLTVDKSRWQQGNVFSCSVMHEALHNHYTQKSLSLSPGK

>Heavy chain of Ab#N
                                     (SEQ ID NO.: 14)
EVQLVQSGAEVKKPGASVKVSCKASGYTFTSYYMYWVRQAPGQGLEWIGG INPSNgGTNFNEKFKNRATLTVDKSTSTAYMELSSLRSEDTAVYYCTREG

NPYYTMNYWGQGTLVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFEGGPSVFLFPPKPKDTL
```

```
MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK

>Heavy chain of Ab#P
                                         (SEQ ID NO.: 15)
EVQLVQSGAEVKKPGASVKVSCKASGYTFTSYYMYWVRQAPGQGLEWIGG INPSNaGTNFNEKFKNRATLTVDKSTSTAYMELSSLRSEDTAVYYCTREG

NPYYTMNYWGQGTLVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFEGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK

>Heavy chain of Ab#R
                                         (SEQ ID NO.: 16)
EVQLVQSGAEVKKPGASVKVSCKASGYTFTSYYMYWVRQAPGQGLEWIGG INPSNgGTNFNEKFKNRATLTVDKSTSTAYMELSSLRSEDTAVYYCTREG

NPYYTMNYWGQGTLVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEAAGGPSVFLFPPKPKDTL

MISRTPEVTCVVVDVSQEDPEVQFNVVYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK

>Heavy chain of Ab#T
                                         (SEQ ID NO.: 17)
EVQLVQSGAEVKKPGASVKVSCKASGYTFTSYYMYWVRQAPGQGLEWIGG INPSNaGTNFNEKFKNRATLTVDKSTSTAYMELSSLRSEDTAVYYCTREG

NPYYTMNYWGQGTLVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEAAGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK
```

In some embodiments, the anti-Cx43 antibody can have the following light chain sequence (wherein the bold portion corresponds to the variable domain and the non-bolded portion corresponds to the constant region):

```
>Light chain of Ab#F, Ab#H, Ab#J, Ab#L, Ab#N,
Ab#P, Ab#R, Ab#T
                                         (SEQ ID NO.: 18)
DVVMTQSPLSLPVTIGQPASISCKSSQSLLESDGKTYLNWLQQRPGQSPR

RLIYLVSKLDSGVPDRFSGSGSGTDFTLKISRVEAEDVGVYYCWQGTHFP

WTFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC
```

In yet another embodiment, the anti-Cx43 antibody can comprise a mixture, or cocktail, of two or more anti-Cx43 antibodies, each of which binds to the same or different epitope on Cx43.

In some embodiments, a bispecific antibody can be made in which at least one of the specificities is an anti-Cx43 antibody or antigen-binding fragment thereof disclosed herein. The other specificity can be directed to another target implicated in the disease being treated.

In one aspect, use of Cx43 ligand for the manufacture of a medicament is provided. In another aspect, a method of suppressing tumor growth and/or metastasis in a patient is provided, the method comprising administering to the patient an effective amount of a Cx43 ligand.

Preparation of Anti-Cx43 Antibodies

Anti-Cx43 antibodies can be made using various methods generally known in the art. For example, phage display technology can be used to screen a human antibody library, to produce a fully human monoclonal antibody for therapy. High affinity binders can be considered candidates for neutralization studies. Alternatively, a conventional monoclonal approach can be used, in which mice or rabbits can be immunized with the human protein, candidate binders identified and tested, and a humanized antibody ultimately produced by engrafting the combining sites of heavy and light chains into a human antibody encoding sequence.

Antibodies typically comprise two identical pairs of polypeptide chains, each pair having one full-length "light" chain (typically having a molecular weight of about 25 kDa) and one full-length "heavy" chain (typically having a molecular weight of about 50-70 kDa). The amino-terminal portion of each chain typically includes a variable region of about 100 to 110 or more amino acids that typically is responsible for antigen recognition. The carboxy-terminal portion of each chain typically defines a constant region responsible for effector function. The variable regions of each of the heavy chains and light chains typically exhibit the same general structure comprising four relatively conserved framework regions (FR) joined by three hyper variable regions, also called complementarity determining regions or CDRs. The CDRs from the two chains of each pair typically are aligned by the framework regions, which alignment may enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of *Kabat Sequences of Proteins of Immunological Interest* (1987 and 1991, National Institutes of Health, Bethesda, Md.), Chothia & Lesk, 1987, *J. Mol. Biol.* 196: 901-917, or Chothia et al., 1989, *Nature* 342:878-883).

Antibodies became useful and of interest as pharmaceutical agents with the development of monoclonal antibodies. Monoclonal antibodies are produced using any method that produces antibody molecules by continuous cell lines in culture. Examples of suitable methods for preparing monoclonal antibodies include the hybridoma methods of Kohler et al. (1975, *Nature* 256:495-497) and the human B-cell hybridoma method (Kozbor, 1984, *J. Immunol.* 133:3001; and Brodeur et al., 1987, *Monoclonal Antibody Production Techniques and Applications*, Marcel Dekker, Inc., New York, pp. 51-63).

Monoclonal antibodies may be modified for use as therapeutics. One example is a "chimeric" antibody in which a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Other examples are fragments of such antibodies, so long as they exhibit the desired biological activity. See, U.S. Pat. No. 4,816,567; and Morrison et al. (1985), *Proc. Natl. Acad. Sci. USA* 81:6851-6855. A related development is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass.

Another development is the "humanized" antibody. Methods for humanizing non-human antibodies are well known in the art (see U.S. Pat. Nos. 5,585,089, and 5,693,762; see also Cécile Vincke et al. J. Biol. Chem. 2009; 284:3273-3284 for humanization of llama antibodies). Generally, a humanized antibody is produced by a non-human animal, and then certain amino acid residues, typically from non-antigen recognizing portions of the antibody, are modified to be homologous to said residues in a human antibody of corresponding isotype. Humanization can be performed, for example, using methods described in the art (Jones et al., 1986, *Nature* 321:522-525; Riechmann et al., 1988, *Nature* 332:323-327; Verhoeyen et al., 1988, *Science* 239:1534-1536), by substituting at least a portion of a rodent variable region for the corresponding regions of a human antibody.

More recent is the development of human antibodies without exposure of antigen to human beings ("fully human antibodies"). Using transgenic animals (e.g., mice) that are capable of producing a repertoire of human antibodies in the absence of endogenous mouse immunoglobulin production, such antibodies are produced by immunization with an antigen (typically having at least 6 contiguous amino acids), optionally conjugated to a carrier. See, for example, Jakobovits et al., 1993, *Proc. Natl. Acad Sci. USA* 90:2551-2555; Jakobovits et al., 1993, *Nature* 362:255-258; and Bruggermann et al., 1993, *Year in Immunol.* 7:33. In one example of these methods, transgenic animals are produced by incapacitating the endogenous mouse immunoglobulin loci encoding the mouse heavy and light immunoglobulin chains therein, and inserting loci encoding human heavy and light chain proteins into the genome thereof. Partially modified animals, which have less than the full complement of modifications, are then cross-bred to obtain an animal having all of the desired immune system modifications. When administered an immunogen, these transgenic animals produce antibodies that are immunospecific for these antigens having human (rather than murine) amino acid sequences, including variable regions. See PCT Publication Nos. WO96/33735 and WO94/02602, incorporated by reference. Additional methods are described in U.S. Pat. No. 5,545,807, PCT Publication Nos. WO91/10741, WO90/04036, and in EP 546073B1 and EP 546073A1, incorporated by reference. Human antibodies may also be produced by the expression of recombinant DNA in host cells or by expression in hybridoma cells as described herein.

In some embodiments, phage display technology may be used to screen for therapeutic antibodies. In phage display, antibody repertoires can be displayed on the surface of filamentous bacteriophage, and the constructed library may be screened for phages that bind to the immunogen. Antibody phage is based on genetic engineering of bacteriophages and repeated rounds of antigen-guided selection and phage propagation. This technique allows in vitro selection of Cx43 monoclonal antibodies. The phage display process begins with antibody-library preparation followed by ligation of the variable heavy ($V_H$) and variable light ($V_L$) PCR products into a phage display vector, culminating in analysis of clones of monoclonal antibodies. The $V_H$ and $V_L$ PCR products, representing the antibody repertoire, are ligated into a phage display vector (e.g., the phagemid pComb3X) that is engineered to express the $V_H$ and $V_L$ as an scFv fused to the pIII minor capsid protein of a filamentous bacteriophage of *Escherichia coli* that was originally derived from the M13 bacteriophage. However, the phage display vector pComb3X does not have all the other genes necessary to encode a full bacteriophage in *E. coli*. For those genes, a helper phage is added to the *E. coli* that are transformed with the phage display vector library. The result is a library of phages, each expressing on its surface a Cx43 monoclonal antibody and harboring the vector with the respective nucleotide sequence within. The phage display can also be used to produce the Cx43 monoclonal antibody itself (not attached to phage capsid proteins) in certain strains of *E. Coli*. Additional cDNA is engineered, in the phage display vector, after the $V_L$ and $V_H$ sequences to allow characterization and purification of the mAb produced. Specifically, the recombinant antibody may have a hemagglutinin (HA) epitope tag and a polyhistidine to allow easy purification from solution.

Diverse antibody phage libraries are produced from ~$10^8$ independent *E. coli* transformants infected with helper phage. Using bio-panning, a library can screened for phage binding to the immunogen sequence listed above, or a fragment thereof, through the expressed surface of the monoclonal antibody. Cyclic panning allows for pulling out potentially very rare antigen-binding clones and consists of multiple rounds of phage binding to antigen (immobilized on ELISA plates or in solution on cell surfaces), washing, elution, and reamplification of the phage binders in *E. coli*. During each round, specific binders are selected out from the pool by washing away non-binders and selectively eluting binding phage clones. After three or four rounds, highly specific binding of phage clones through their surface Cx43 monoclonal antibody is characteristic for directed selection on the immobilized immunogen.

Another method is to add a C-terminal His tag, suitable for purification by affinity chromatography, to the immunogen sequence listed above. Purified protein can be inoculated into mice together with a suitable adjuvant. Monoclonal antibodies produced in hybridomas can be tested for binding to the immunogen, and positive binders can be screened as described in the assays herein.

Fully human antibodies can also be produced from phage-display libraries (as disclosed in Hoogenboom et al., 1991, *J. Mol. Biol.* 227:381; and Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in PCT Publication No. WO99/10494, incorporated by reference, which describes the isolation of high affinity and functional agonistic antibodies for MPL- and msk-receptors using such an approach.

Nucleotide sequences encoding the above antibodies can be determined. Thereafter, chimeric, CDR-grafted, humanized, and fully human antibodies also may be produced by recombinant methods. Nucleic acids encoding the antibodies can be introduced into host cells and expressed using materials and procedures generally known in the art.

The disclosure provides antibodies against Cx43. Preferably, the antibodies bind Cx43. In preferred embodiments, the disclosure provides nucleotide sequences encoding, and amino acid sequences comprising, heavy and light chain immunoglobulin molecules, particularly sequences corresponding to the variable regions thereof. In preferred embodiments, sequences corresponding to CDRs, specifically from CDR1 through CDR3, are provided. In additional embodiments, the disclosure provides hybridoma cell lines expressing such immunoglobulin molecules and monoclonal antibodies produced therefrom, preferably purified human monoclonal antibodies against human Cx43.

The CDRs of the light and heavy chain variable regions of anti-Cx43 antibodies of the disclosure can be grafted to framework regions (FRs) from the same, or another, species. In certain embodiments, the CDRs of the light and heavy chain variable regions of anti-Cx43 antibody may be grafted to consensus human FRs. To create consensus human FRs, FRs from several human heavy chain or light chain amino acid sequences are aligned to identify a consensus amino acid sequence. The FRs of the anti-Cx43 antibody heavy chain or light chain can be replaced with the FRs from a different heavy chain or light chain. Rare amino acids in the FRs of the heavy and light chains of anti-Cx43 antibody typically are not replaced, while the rest of the FR amino acids can be replaced. Rare amino acids are specific amino acids that are in positions in which they are not usually found in FRs. The grafted variable regions from anti-Cx43 antibodies of the disclosure can be used with a constant region that is different from the constant region of anti-Cx43 antibody. Alternatively, the grafted variable regions are part of a single chain Fv antibody. CDR grafting is described, e.g., in U.S. Pat. Nos. 6,180,370, 5,693,762, 5,693,761, 5,585,089, and 5,530,101, which are hereby incorporated by reference for any purpose.

In some embodiments, antibodies of the disclosure can be produced by hybridoma lines. In these embodiments, the antibodies of the disclosure bind to Cx43 with a dissociation constant ($K_D$) of between approximately 4 pM and 1 µM. In certain embodiments of the disclosure, the antibodies bind to Cx43 with a $K_D$ of less than about 100 nM, less than about 50 nM or less than about 10 nM.

In embodiments, the antibodies of the present disclosure are of the IgG1, IgG2, IgG3, or IgG4 isotype, such as the IgG1 isotype. In certain embodiments, the antibodies comprise a human kappa or lambda light chain and a human IgG1, IgG2, or IgG4 heavy chain. In embodiments, the variable regions of the antibodies are ligated to a constant region of the IgG1, IgG2, or IgG4 isotype. In particular embodiments, the variable regions of the antibodies are ligated to a constant region other than the constant region for the IgG1, IgG2, or IgG4 isotype. In certain embodiments, the antibodies of the disclosure have been cloned for expression in mammalian cells.

In alternative embodiments, antibodies of the disclosure can be expressed in cell lines other than hybridoma cell lines. In these embodiments, sequences encoding particular antibodies can be used for transformation of a suitable mammalian host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art. Such procedures are exemplified by U.S. Pat. Nos. 4,399,216, 4,912,040, 4,740,461, and 4,959,455 (all of which are hereby incorporated herein by reference for any purpose). Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene-mediated transfection, protoplast fusion, electroporation, encapsulation of the polynucleotide(s) in liposomes, and direct microinjection of the DNA into nuclei.

According to certain embodiments of the methods of the disclosure, a nucleic acid molecule encoding the amino acid sequence of a heavy chain constant region, a heavy chain variable region, a light chain constant region, or a light chain variable region of a Cx43 antibody of the disclosure is inserted into an appropriate expression vector using standard ligation techniques. In a preferred embodiment, the Cx43 antibody heavy or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see, Goeddel (ed.), 1990, *Meth. Enzymol.* Vol. 185, Academic Press. N.Y.

Typically, expression vectors used in any of the host cells can contain sequences for plasmid maintenance and for cloning and expression of exogenous nucleotide sequences. Such sequences typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. These sequences are well known in the art.

Expression vectors of the disclosure may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well know n to one skilled in the art.

After the vector has been constructed and a nucleic acid molecule encoding light chain or heavy chain or light chain and heavy chain comprising an anti-Cx43 antibody has been inserted into the proper site of the vector, the completed vector may be inserted into a suitable host cell for amplification and/or polypeptide expression. The transformation of an expression vector for an anti-Cx43 antibody into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., supra.

The host cell, when cultured under appropriate conditions, synthesizes an anti-Cx43 antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), including but not limited to Chinese hamster ovary (CHO) cells, human embryonic kidney cells (HEK), HeLa cells, baby hamster kidney (BHK) cells, monkey kidney cells (COS), human hepatocellular carcinoma cells (e.g., Hep G2), and a number of other cell lines. In certain embodiments, one may select cell lines by determining which cell lines have high expression levels and produce antibodies with constitutive Cx43 binding properties. In another embodiment, one may select a cell line from the B cell lineage that does not make its own antibody but has a capacity to make and secrete a heterologous antibody (e.g., mouse myeloma cell lines NS0 and SP2/0).

Epitope Mapping and Related Technologies

The present disclosure provides anti-Cx43 antibodies, which interact with one or more amino acids found within one or more domains, e.g., extracellular loops, of the Cx43 molecule. The epitope to which the antibodies bind may include one or more contiguous sequences of 2 or more (e.g., 2, 3, 4, 5, 6, 7, 8, 9, or more) amino acids located within one or more extracellular loops. Alternatively or additionally, the epitope may include 1 or more non-contiguous amino acids (or amino acid sequences) located within one or more extracellular loops (e.g. a conformational epitope).

Various techniques known to persons of ordinary skill in the art can be used to determine whether an antibody "Interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor,. N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496).

Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to son the antibodies of the invention into groups of antibodies binding different epitopes.

The present disclosure provides anti-Cx43 antibodies that bind to the same epitope, or a portion of the epitope. Likewise, the present disclosure also includes anti-Cx43 antibodies that compete for binding to Cx43 or a fragment thereof with any of the specific exemplary antibodies described herein. For example, the present disclosure includes anti-Cx43 antibodies that cross-compete for binding to Cx43 with one or more antibodies obtained from those antibodies described herein.

One can easily determine whether an antibody binds to the same epitope as, or competes for binding with, a reference anti-Cx43 antibody by using routine methods known in the art. For example, to determine if a test antibody binds to the same epitope as a reference anti-Cx43 antibody of the invention, the reference antibody can be allowed to bind to Cx43 or peptide under saturating conditions. Next, the ability of a test antibody to bind to the Cx43 molecule is assessed. If the test antibody is able to bind to Cx43 following saturation binding with the reference anti-Cx43 antibody, it can be concluded that the test antibody binds to a different epitope than the reference anti-Cx43 antibody. On the other hand, if the test antibody is not able to bind to the Cx43 following saturation binding with the reference anti-Cx43 antibody, then the test antibody may bind, to the same epitope as the epitope bound by the reference anti-Cx43 antibody of the present disclosure.

To determine if an antibody competes for binding with a reference anti-Cx43 antibody, the above-described binding methodology can be performed in two orientations: In a first orientation, the reference antibody can be allowed to bind to Cx43 under saturating conditions followed by assessment of binding of the test antibody to the Cx43 molecule. In a second orientation, the test antibody can be allowed to bind to a Cx43 molecule under saturating conditions followed by assessment of binding of the reference antibody to the Cx43 molecule. If, in both orientations, only the first (saturating) antibody is capable of binding to the Cx43 molecule, then it is concluded that the test antibody and the reference antibody compete for binding to Cx43. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be earned out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

In various embodiments, provided herein is an antibody that binds an epitope located within, partially or entirely, the amino acid sequence of FLSRPTEKTI (SEQ ID NO: 19). In some embodiments, the epitope can comprise one or more amino acids selected from the group consisting of F1, S3, R4, P5, T6, E7, K8, T9 and 110 of SEQ ID NO: 19. In one embodiment, the epitope consists of F1, S3, R4, P5, T6, E7, K8, T9 and 110 of SEQ ID NO: 19. In some embodiments, the epitope can include all ten amino acids of SEQ ID NO: 19. In certain embodiments, the epitope consists of ail ten amino acids of SEQ ID NO: 19.

Pharmaceutical Compositions and Use Thereof

In another aspect, pharmaceutical compositions are provided that can be used in the methods disclosed herein, i.e., pharmaceutical compositions for promoting opening of Cx43 hemichannels in osteocytes, preferably for treating cancer, cancer metastasis, osteosarcoma, osteoporosis, or osteopenia.

In some embodiments, the pharmaceutical composition comprises a Cx43 ligand and a pharmaceutically acceptable carrier. The Cx43 ligand can be formulated with the pharmaceutically acceptable earner into a pharmaceutical composition. Additionally, the pharmaceutical composition can include, for example, instructions for use of the composition for the treatment of patients to promote opening of Cx43 hemichannels in osteocytes, preferably for treating cancer, cancer metastasis, osteosarcoma, osteoporosis, or osteopenia.

In one embodiment, the Cx43 ligand can be an anti-Cx43 antibody or antigen-binding fragment thereof.

As used herein, "pharmaceutically acceptable earner" includes any and all solvents, dispersion media, coatings, antibacterial and antifungal agents, isotonic and absorption delaying agents, buffers, and other excipients that are physiologically compatible. Preferably, the carrier is suitable for parenteral, oral, or topical administration. Depending on the route of administration, the active compound, e.g., small molecule or biologic agent, may be coated in a material to protect the compound from tire action of acids and other natural conditions that may inactivate the compound.

Pharmaceutically acceptable carriers include sterile aqueous solutions or dispersions and sterile powders for the extemporaneous preparation of sterile injectable solutions or dispersion, as well as conventional excipients for the preparation of tablets, pills, capsules and the like. The use of such media and agents for the formulation of pharmaceutically active substances is known in the art. Except insofar as any conventional media or agent is incompatible with the active compound, use thereof in the pharmaceutical compositions provided herein is contemplated. Supplementary active compounds can also be incorporated into the compositions.

A pharmaceutically acceptable carrier can include a pharmaceutically acceptable antioxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous earners which may be employed in the pharmaceutical compositions provided herein include water, ethanol, polyols (such as glycerol, propylene glycol, polyethylene glycol, and the like), and suitable mixtures thereof, and injectable organic esters, such as ethyl oleate. When required, proper fluidity can be maintained, for example, by the use of coating materials, such as lecithin, by the maintenance of the required particle size in the case of dispersions, and by the use of surfactants. In many cases, it may be useful to include isotonic agents, for example, sugars, poly alcohols such as mannitol, sorbitol, or sodium chloride in the composition. Prolonged absorption of the injectable compositions can be brought about by including in the composition an agent that delays absorption, for example, monostearate salts and gelatin.

These compositions may also contain functional excipients such as preservatives, wetting agents, emulsifying agents and dispersing agents.

Therapeutic compositions typically must be sterile, non-phylogenic, find stable under the conditions of manufacture and storage. The composition can be formulated as a solution, microemulsion, liposome, or other ordered structure suitable to high drug concentration.

Sterile injectable solutions can be prepared by incorporating the active compound in the required amount in an appropriate solvent with one or a combination of ingredients enumerated above, as required, followed by sterilization, e.g., by microfiltration. Generally, dispersions are prepared by incorporating the active compound into a sterile vehicle that contains a basic dispersion medium and the required other ingredients from those enumerated above. In the case of sterile powders for tire preparation of sterile injectable solutions, methods of preparation include vacuum drying and freeze-drying (lyophilization) that yield a powder of the active ingredient plus any additional desired ingredient from a previously sterile-filtered solution thereof. The active agent(s) may be mixed under sterile conditions with additional pharmaceutically acceptable carrier(s), and with any preservatives, buffers, or propellants which may be required.

Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions comprising a Cx43 ligand can be administered alone or in combination therapy. For example, the combination therapy can include a composition provided herein comprising a Cx43 ligand and at least one or more additional therapeutic agents, such as one or more chemotherapeutic agents known in the art, discussed in further detail below. Pharmaceutical compositions can also be administered in conjunction with radiation therapy and/or surgery.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation.

Exemplary dosage ranges for administration of an antibody include: 10-1000 mg (antibody)/kg (body weight of the patient), 10-800 mg/kg, 10-600 mg/kg, 10-400 mg/kg, 10-200 mg/kg, 30-1000 mg/kg, 30-800 mg/kg, 30-600 mg/kg, 30-400 mg/kg, 30-200 mg/kg, 50-1000 mg/kg, 50-800 mg/kg, 50-600 mg/kg, 50-400 mg/kg, 50-200 mg/kg, 100-1000 mg/kg, 100-900 mg/kg, 100-800 mg/kg, 100-700 mg/kg, 100-600 mg/kg, 100-500 mg/kg, 100-400 mg/kg, 100-300 mg/kg and 100-200 mg/kg. Exemplary dosage schedules include once every three days, once every five days, once every seven days (i.e., once a week), once every 10 days, once every 14 days (i.e., once every two weeks), once every 21 days (i.e., once every three weeks), once every 28 days (i.e., once every four weeks) and once a month.

It may be advantageous to formulate parenteral compositions in unit dosage form for ease of administration and uniformity of dosage. Unit dosage form as used herein refers to physically discrete units suited as unitary dosages for the patients to be treated; each unit contains a predetermined quantity of active agent calculated to produce the desired therapeutic effect in association with any required pharmaceutical carrier. The specification for unit dosage forms are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions disclosed herein may be varied so as to obtain an amount of the active ingredient which is effective to achieve the desired therapeutic response for a particular patient, composition, and mode of administration, without being toxic to the patient. "Parenteral" as used herein in the context of administration means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The phrases "parenteral administration" and "administered parenterally" as used herein refer to modes of administration other than enteral (i.e., via the digestive tract) and topical administration, usually by injection or infusion, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Intravenous injection and infusion are often (but not exclusively) used for antibody administration.

When agents provided herein are administered as pharmaceuticals, to humans or animals, they can be given alone or as a pharmaceutical composition containing, for example, 0.001 to 90% (e.g., 0.005 to 70%. e.g., 0.01 to 30%) of active ingredient in combination with a pharmaceutically acceptable carrier.

In certain embodiments, the methods and uses provided herein for promoting opening of Cx43 hemichannels in osteocytes, preferably for treating cancer, cancer metastasis, osteosarcoma, osteoporosis, or osteopenia, can comprise administration of a Cx43 ligand and at least one additional anti-cancer agent that is not a Cx43 ligand.

In one embodiment, the at least one additional anti-cancer agent composes at least one chemotherapeutic drug. Non-limiting examples of such chemotherapeutic drugs include platinum-based chemotherapy drugs (e.g., cisplatin, carboplatin), taxanes (e.g., paclitaxel (Taxol®), docetaxel (Taxotere®), EndoTAG-1™ (a formulation of paclitaxel encapsulated in positively charged lipid-based complexes; MediGene), Abraxane® (a formulation of paclitaxel bound to albumin)), tyrosine kinase inhibitors (e.g., imatinib/Gleevec®, sunitinib/Sutent®, dasatinib/Sprycel®), and combinations thereof.

In another embodiment, the at least one additional anti-cancer agent comprises an EGFR inhibitor, such as an anti-EGFR antibody or a small molecule inhibitor of EGFR signaling. An exemplarsy anti-EGFR antibody is cetuximab (Erbitux®). Cetuximab is commercially available from ImClone Systems Incorporated. Other examples of anti-EGFR antibodies include matuzumab (EMD72000), panitumumab (Vectibix®; Amgen); nimotuzumab (TheraCIM™) and mAb 806. An exemplary small molecule inhibitor of the EGFR signaling pathway is gefitinib (Iressa®), which is commercially available from AstraZeneca and Teva. Other examples of small molecule inhibitors of the EGFR signaling pathway include erlotinib HCL (OSI-774; Tarceva®, OSI Pharma); lapatinib (Tykerb®, GlaxoSmithKline); canertinib (canertinib dihydrochloride, Pfizer); pelitinib (Pfizer); PKI-166 (Novartis); PD 158780; and AG 1478 (4-(3-Chloroanillino)-6,7-dimethoxyquinazoline).

In yet another embodiment, the at least one additional anti-cancer agent comprises a VEGF inhibitor. An exemplary VEGF inhibitor comprises an anti-VEGF antibody, such as bevacizumab (Avastatin®; Genentech).

In still another embodiment, the at least one additional anti-cancer agent comprises an anti-ErbB2 antibody. Suitable anti-ErbB2 antibodies include trastuzumab and pertuzumab.

In one aspect, the improved effectiveness of a combination according to the disclosure can be demonstrated by achieving therapeutic synergy.

The term "therapeutic synergy" is used when the combination of two products at given doses is more efficacious than the best of each of the two products alone at the same doses. In one example, therapeutic synergy can be evaluated by comparing a combination to the best single agent using estimates obtained from a two-way analysis of variance with repeated measurements (e.g., time factor) on parameter tumor volume.

The term "additive" refers to when the combination of two or more products at given doses is equally efficacious than the sum of the efficacies obtained with of each of the two or more products, whilst the term "superadditive" refers to when the combination is more efficacious than the sum of the efficacies obtained with of each of the two or more products.

Another measure by which effectiveness (including effectiveness of combinations) can be quantified is by calculating the $\log_{10}$ cell kill, which is determined according to the following equation: $\log_{10}$ cell kill=T-C(days)/3.32×$T_d$ in winch T-C represents the delay in growth of the cells, which is the average time, in days, for the tumors of the treated group (T) and the tumors of the control group (C) to have reached a predetermined value (1 g, or 10 mL, for example), and $T_d$ represents the time, in days necessary for the volume of the tumor to double in the control annuals. When applying tins measure, a product is considered to be active if $\log_{10}$ cell kill is greater than or equal to 0.7 and a product is considered to be very active if $\log_{10}$ cell kill is greater than 2.8.

Using this measure, a combination, used at its own maximum tolerated dose, in winch each of the constituents is present at a dose generally less than or equal to its maximum tolerated dose, exhibits therapeutic synergy when the $\log_{10}$ cell kill is greater than the value of the $\log_{10}$ cell kill of the best constituent when it is administered alone. In an exemplary case, the $\log_{10}$ cell kill of the combination exceeds the value of the $\log_{10}$ cell kill of the best constituent of the combination by at least one log cell kill.

Disclosed herein are compositions and methods for providing cancer therapy. The method can include promoting opening of Cx43 hemichannels in osteocytes in a subject in need thereof. Cx43 modulation (e.g., an anti-Cx43 antibody) can be used as a stand-alone cancer therapy, or in conjunction with other cancer therapy.

Also provided herein is a method for promoting opening of Cx43 hemichannels in osteocytes, preferably for treating cancer, cancer metastasis, osteosarcoma, osteoporosis, or osteopenia, comprising administering any one or more of the anti-Cx43 antibodies disclosed herein in a subject in need thereof.

In various embodiments, the methods disclosed herein can include administering to the subject an effective amount of anti-Cx43 antibody or antigen-binding fragment thereof. In general, the effective amount can be administered therapeutically and/or prophylactically.

Treatment can be suitably administered to subjects, particularly humans, suffering from, having, susceptible to, or at risk of developing such cancer. Determination of those subjects "at risk" can be made by any objective or subjective determination by a diagnostic test or opinion of a subject or health care provider (e.g., genetic test, enzyme or protein marker, family history, and the like). Identifying a subject in need of such treatment can be in the judgment of a subject or a health care professional and can be subjective (e.g. opinion) or objective (e.g. measurable by a test or diagnostic method).

Administration of the Formulation

The formulations of the present disclosure, including but not limited to reconstituted and liquid formulations, are administered to a mammal in need of treatment with the anti-Cx43 antibodies, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

In embodiments, the formulations are administered to the mammal by intravenous or subcutaneous (i.e., beneath the skin) administration. For such purposes, the formulation may be injected using a syringe. How ever, other devices for administration of the formulation are available such as injection devices (e.g., the INJECT-EASE™ and GENJECT™ devices); injector pens (such as the GENPEN™); auto-injector devices, needleless devices (e.g., MEDIJECTOR™ and BIOJECTOR™); and subcutaneous patch delivery systems.

In a specific embodiment, the present disclosure is directed to kits for a single dose-administration unit. Such kits comprise a container of an aqueous formulation of therapeutic protein or antibody, including both single or multi-chambered pre-filled syringes. Exemplary pre-filled syringes are available from Vetter GmbH, Ravensburg, Germany.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to anti-Cx43 antibody, the format of the formulation used, and the discretion of the attending physician. The anti-Cx43 antibody is suitably administered to the patient at one time or over a series of treatments and may be administered to the patient at any time from diagnosis onwards. The anti-Cx43 antibody may be administered as the sole treatment or in conjunction with other drugs or therapies useful in treating the condition in question.

For anti-Cx43 antibodies, an initial candidate dosage can range from about 0.1-100 or 1-20 mg/kg for administration to the patient, which can take the form of one or more separate administrations. However, other dosage regimens may be useful. The progress of such therapy is easily monitored by conventional techniques.

According to certain embodiments of the present disclosure, multiple doses of an anti-Cx43 antibody (or a pharmaceutical composition comprising a combination of an anti-Cx43 antibody and any of the additional therapeutically active agents mentioned herein) may be administered to a subject over a defined tune course. The methods according to this aspect of the disclosure comprise sequentially administering to a subject multiple doses of an anti-Cx43 antibody of the disclosure. As used herein, "sequentially administering" means that each dose of anti-Cx43 antibody is administered to the subject at a different point in time, e.g., on different days separated by a predetermined interval (e.g., hours, days, weeks or months). The present disclosure includes methods which comprise sequentially administering to the patient a single initial dose of an anti-Cx43 antibody, followed by one or more secondary doses of the anti-Cx43 antibody, and optionally followed by one or more tertiary doses of the anti-Cx43 antibody. The anti-Cx43 antibody may be administered at a dose of between 0.1 mg/kg to about 100 mg/kg.

The terms "initial dose," "secondary doses," and "tertian doses," refer to the temporal sequence of administration of the anti-Cx43 antibody of the disclosure. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-Cx43 antibody, but generally may differ from one another in terms of frequency of administration. In certain embodiments, however, the amount of anti-Cx43 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3 1/2, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-Cx43 antibody which is administered to a patient prior to the administration of the very next dose in the sequence with no intervening doses.

The methods according to this aspect of the disclosure may comprise administering to a patient any number of secondary and/or tertiary doses of an anti-Cx43 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which –10 or 2-6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of, e.g., once a month (e.g., two, three, four, or more loading doses administered once a month), then the maintenance doses may be administered to the patient once even five weeks, once even six weeks, once every seven weeks, once every eight weeks, once every ten weeks, once every twelve weeks, etc.).

EXAMPLES

The following examples, including the experiments conducted and results achieved are provided for illustrative purposes only and are not to be construed as limiting the disclosure.

Example 1: Binding Affinity

Optimized sequences were tested for binding affinity to Cx43 according to the following protocol.
1. Desorb Biacore T200
2. Insert new CM5 chip
3. Prime 3X with HBS-EP+ buffer (10 mM Hepes, 150 mM NaCl, 3 mM EDTA, 0.05% surfactant P20 [tween20])
4. Precondition: Start a new sensorgram at 100 ul/min. Inject 10 ul each of 2× 100 mM HCl, 2× 50 mM NaOH, 2× 0.5% SDS using regen command with high viscosity solution (extra clean). This cleans and prepares the chip for coupling. Only do this on a blank chip, never after a protein has been attached.
5. Amine Couple Anti-Human IgG Fc (GE: BR-1008-39) to each surface you will use (including reference surface) separately following instructions provided with the GE Human Antibody capture kit. Briefly, the Mab is diluted to 25 ug/ml in 10 mM Sodium Acetate pH 5. Start a new sensorgram at 5 ul/min. In quick succession activate 7' with NHS/EDC, inject Mab 7', and block with ethanolamine 7'. Typically obtained 10,000-12,000 RUs/surface. Follow this with 10 regenerations with 3 M $MgCl_2$ for 30 sec at 20 ul/min). (Note experiments with Mouse IgG were done similarly, except that we used the GE Mouse Antibody Capture Kit (GE: BR-1008-38). The only difference is that the anti-mouse IgG antibody is coupled at 30 ug/ml and regenerated w 10 mM Glycine-HCl pH 1.7 for 3 min at 20 ul/min).
6. Normalize followed by 1× Prime in HBS-EP+ buffer.
7. Experiments were then performed immediately after amine coupling. When there was significant time between experiments, the chip was removed and stored at 4 degrees C. When the chip was put back into the instrument, this was followed by 3× prime with HBS-EP+, Normalize, 1× Prime with HBS-EP+.

A program was written using the following parameters:
Overview:
  Buffer=HBS-EP+
  Flow Rate=100 ul/min
  Data Collection Rate=1 Hz
  Sample Compartment Temp=15 degrees C. (this is the temp the samples are kept at prior to injection)
  Assay Run Temp=25 degrees C.
  Dual Detection, Fc2-Fc1
For each cycle of the experiment:
  a. Capture Mab Ab #K on FC2 by injecting 5 ug/ml Mab 180 s at 5 ul/min on FC2 only with extra wash after injection with 1% Tween20.
  b. Inject 1 M NaCl 30 s at 30 ul/min on both FCs, followed by an extra buffer wash and 180 s stabilization.
  c. Inject Sample (peptide) w High Performance Injection for 210 s at 100 ul/min, w 300 s of dissociation on both FCs, followed by an extra buffer wash and 60 sec stabilization.

e. Regenerate both surfaces with 3 M MgCl$_2$ for 30 s at 20 ul/min selecting high viscosity solution followed by a buffer wash and 60 sec stabilization.

The cycles were programmed as follows:
1. 10 startup injections of buffer to stabilize instrument.
2. A concentration series of each peptide (PEP1, PEP2, PEP3): 0, 4 nM, 12 nM, 37 nM, 111 nM, 333 nM, 1000 nM Cycles 1-10 startup
Cycles 11-17 PEP1 (914)
Cycles 18-24 PEP2 (915)
Cycles 25-31 PEP3 (916)
Cycles 32-38 PEP1 (914)
Cycles 39-45 PEP2 (915)
Cycles 46-52 PEP3 (916)
Cycles 53-59 PEP1 (914)
Cycles 60-66 PEP2 (915)
Cycles 67-73 PEP3 (916)

Data Analysis

Data was analyzed using T200 evaluation software 2.0. (Fc2-Fc1) data from each set of triplicates were globally fit to either a 1:1 Binding Kinetic Model, or Steady State Affinity model since equilibrium was reached under conditions optimal for kinetics. Results obtained with both methods were similar.

The above protocol was followed for all the experiments in which the Mab was captured on the surface of a CM5 chip.

A CAP chip was also used according to the following protocol:
1. CAP chip from Bitoin CAPture kit from GE Healthcare (28920234) was prepared according to manufacturer's instructions. Briefly it was docked in the instrument (T200) and triple primed w running buffer (HBS-EP+) and hydrated with running buffer in standby mode overnight. It was then conditioned by 3×60 s injections at 30 ul/min with regeneration solution (6M GuHCl, 250 mM NaOH). This was followed by 1× normalize and 1× prime. It was then ready for an experiment. A program was written using the following parameters:

Overview:
Buffer=HBS-EP+
Flow Rate=100 ul/min
Data Collection Rate=1 Hz
Sample Compartment Temp=15 degrees C. (this is the temp the samples are kept at prior to injection)
Assay Run Temp=25 degrees C.
Dual Detection, Fc4-Fc3

For each cycle of the experiment:
a. Capture Biotin Capture Reagent on Fc3 and Fc4 by injecting Biotin Capture Reagent from Kit for 300s at 2 ul/min.
b. Capture biotinylated peptide on Fc4 by injecting 3 ug/ml peptide 2 for 120 s at 5 ul/min, followed by an extra buffer wash and 120 s stabilization.
c. Inject Sample (Mab) w High Performance Injection for 210 s at 100 ul/min, w 300 s of dissociation on both Fcs.
d. Regenerate both surfaces with 6M GuHCl, 250 mM NaOH for 120 sec at 30 ul/min (select high viscosity solution) followed by a buffer wash and 120 sec stabilization.

The cycles were programmed as follows:
1. 5 startup injections of buffer to stabilize instrument.
2. A concentration series of each Mab (I or H): 0, 6.2 nM, 18.5 nM, 55.6 nM, 166.7 nM, 500 nM was run.

Cycle 1-5 Startup
Cycle 6-11 Mab I
Cycle 12-17 Mab H
Cycle 18-23 Mab I
Cycle 24-29 Mab H Binding affinity results (Table 1) show that in general binding affinity was at least maintained and in many cases, surprisingly enhanced.

TABLE 1

Binding affinity of various antibodies

| Molecule ID | Kd (M) |
| --- | --- |
| Control | 1.474E−7 |
| Ab#D | 1.985E−7 |
| Ab#F | 3.347E−11 |
| Ab#H | 4.650E−8 |
| Ab#J | 1.260E−8 |
| Ab#L | 1.012E−8 |
| Ab#X | 3.412E−10 |
| Ab#P | 8.582E−9 |
| Ab#R | 4.920E−8 |
| Ab#T | 5.821E−10 |

Example 2. Fc Receptor Binding Analysis

The Fc effector functions are mediated by binding of Fc to receptors. The receptors include FCRI, FCRIIa, FCRIIb, FCRIIIa, FCRIIIb, C1q, and FcRn. It is generally desirable to reduce binding affinities to most of the Fc receptors expect FcRn to minimize potential in-vivo toxicity while maintaining antibody half-life. The following surface plasmon resonance (SPR) and enzyme-linked immunosorbent assay (ELISA) protocols were used to test different Fc receptor binding for various antibodies.

A. FCRI Binding
Experiment: Biacore 8K
Chip: CM5
(1) Immobilization

The activator was prepared by mixing 400 mM EDC and 100 mM NHS immediately prior to injection. The CM5 sensor chip was activated for 420 s with the mixture. 30 μg/mL of THE™ His tag antibody in 10 mM NaAc (pH 4.5) was then injected to channels 1-8 for 400 s at a flow rate of 30 μL/min. The chip was deactivated by 1 M ethanolamine-HCl (GE).

(2) Capturing Ligand and Running Analyte

2 μg/mL CD64 in running buffer (1×HBS-EP+) was injected to Fc2 of channel 1-4 at a flow rate of 10 μL/min for 30 s. 6 concentrations (40, 20, 10, 5, 2.5 and 1.25 nM) of analyte 20170905-Ab #C-02, 20170905-Ab #D-02, 20170908-Ab #G-02, 20170920-Ab #H-02 and running buffer were injected orderly to Fc1-Fc2 of channel 1-4 at a flow rate of 30 μL/min for an association phase of 180, followed by 400 dissociation. Repeat 6 cycles of capturing ligand and running analyte according to analyte concentrations in ascending order. 10 mM glycine pH 1.5 as regeneration buffer was injected following every dissociation phase.

2 μg/mL CD64 in running buffer (1×HBS-EP+) was injected to Fc2 of channel 1-6 at a flow rate of 10 μL/min for 30 s. 8 concentrations (10240, 5120, 2560, 1280, 640, 320, 160 and 80 nM) of analyte 20170907-Ab #K-02, 20170908-Ab #L-02, 20170915-Ab #O-02, 20170919-Ab #P-02, 20170919-Ab #S-02 and 20170920-Ab #T-02 and running buffer were injected orderly to Fc1-Fc2 of channel 1-6 at a flow rate of 30 μL/min for an association phase of 60, followed by 90 dissociation. Repeat 8 cycles of capturing ligand and running analyte according to analyte concentrations in ascending order. 10 mM glycine pH 1.5 as regeneration buffer was injected following every dissociation phase.

(3) Regeneration

The chip was regenerated with 10 mM glycine pH 1.5.

(4) Data Analysis

Surface channels Fc1 without capturing ligand was used as control surface for reference subtraction. Final data of each interaction w as deducted from reference channel and buffer channel data. The experimental data of 20170905-Ab #C-02, 20170905-Ab #D-02, 20170908-Ab #G-02, 20170920-Ab #H-02 binding to CD64 was fitted by 1:1 binding mode. The 10240 nM curves of analyte 20170907-Ab #K-02, 20170908-Ab #L-02, 20170915-Ab #O-02, 20170919-Ab #P-02, 20170919-Ab #S-02 and 20170920-Ab #T-02 were removed to allow a better fit. The relative experimental data was fitted by steady state affinity and shown in Table 2 below.

TABLE 2

FCRI binding

| Analyte | ka (1/Ms) | kd (1/s) | KD (M) | Comment |
|---|---|---|---|---|
| Ab#D | 4.82E+05 | 9.25E−04 | 1.92E−09 | 1:1 binding |
| Ab#H | 5.54E+05 | 3.18E−03 | 5.73E−09 | |
| Ab#L | NA | | 1.62E−06 | steady state affinity |
| Ab#P | | | 2.79E−06 | |
| Ab#T | | | 3.05E−06 | |

1-8 at a flow rate of 10 μL/min for 15 s. Analytes were injected to channel 1-8 respectively. A series of analyte concentrations (seeing Table 3 below) were monitored at a flow rate of 30 μL/min for an association phase of 60 s, followed by 90 s dissociation. 10 mM glycine pH 1.5 as regeneration buffer was injected following every dissociation phase.

TABLE 3

Analyte concentrations

| Analyte | Tested Concentration (nM) |
|---|---|
| Ab#D | 0, 160, 320, 640, 1280, 2560, 5120, 10240 |
| Others | 0, 320, 640, 1280, 2560, 5120, 10240, 20480, 40960 |

(3) Regeneration

The chip was regenerated with 10 mM glycine pH 1.5.

(4) Data Analysis

Surface channels Fc1 without capturing ligand was used as control surface for reference subtraction. Final data of each interaction was deducted from reference channel and buffer channel data. The experimental data of antibodies binding to FcγRIIa, FcγRIIb, FcγRIIIa, and FcγRIIIb was fitted by steady state affinity mode and shown in Table 4 below.

TABLE 4

FcγRIIa, FcγRIIb, FcγRIIIa, and FcγRIIIb binding

| Sample ID | binding to FcγRIIa | binding to FcγRIIb | binding to FcγRIIIa | binding to FcγRIIIb |
|---|---|---|---|---|
| Ab#D | 3.39E−06 | 1.08E−05 | 2.25E−06 | 5.28E−06 |
| Ab#H | 2.12E−05 | 1.89E−05 | no/very weak binding | no/very weak binding |
| Ab#L | no/very weak binding | no/very weak binding | 3.40E−05 | no/very weak binding |
| Ab#P | no/very weak binding | 2.83E−05 | no/very weak binding | no/very weak binding |
| Ab#T | no/very weak binding | no/very weak binding | no/very weak binding | no/very weak binding |

All antibodies showed low or no FCRI binding which is advantageous.

B. Binding to FcγRIIa, FcγRIIb, FcγRIIIa, FcγRIIIb

Experiment: Biacore 8K

Chip: CM5

(1) Immobilization

The activator was prepared by mixing 400 mM EDC and 100 mM NHS immediately prior to injection. The CM5 sensor chip was activated for 420 s with the mixture. 30 μg/mL of THE™ His tag antibody in 10 mM NaAc (pH 4.5) was then injected to channels 1-8 for 400 s at a flow rate of 30 μL/min. The chip was deactivated by 1 M ethanolamine-HCl (GE).

(2) Capturing Ligand and Running Analyte

1 μg/mL FcγRIIa, FcγRIIb, FcγRIIIa, or FcγRIIIb in running buffer (1×HBS-EP+) was injected to Fc2 of channel All antibodies showed low or no FcγRIIa, FcγRIIb, FcγRIIIa, and FcγRIIIb binding which is advantageous.

C. Binding to FcRn

Experiment: Biacore 8K

Chip: CM5

(1) Buffer Exchange

Buffer of human FcRn was exchanged to running buffer (50 mM $Na_2HPO_4$, 50 mM $NaH_2PO_4$, 150 mM NaCl, 0.05% Tween20, pH 6.0) using desalting column according to the instruction manual. The concentration was determined by Nanodrop.

(2) Immobilization

The activator was prepared by mixing 400 mM EDC and 100 mM NHS (GE) immediately prior to injection. The CM5 sensor chip was activated for 420 s with the mixture at a flow rate of 10 μL/min. 5 μg/mL of antibodies in 10 mM NaAc (pH 5.5) were then injected to Fc2 of channel 1-8 respectively at a flow rate of 10 μL/min for 60 s. The relative Fc1 was blocked. The chip was deactivated by 1 Methanolamine-HCl (GE) at a flow rate of 10 μL/min for 420 s.

(2) Running Analyte

Analyte FcRn was injected to channel 1-8 respectively. 8 concentrations of FcRn (0, 93.75, 187.5, 375, 750, 1500, 3000 and 6000 nM) were monitored at a flow rate of 30 μL/min for an association phase of 60 s, followed by 90 s dissociation. After each cycle of interaction analysis, the sensor chip surface was regenerated with 1×PBS (pH 7.4) at a flow rate of 10 μL/min for 30 s.

(3) Regeneration

The chip was regenerated with 1×PBS (pH 7.4).

(4) Data Analysis

Surface channels Fc1 without immobilized antibodies were used as control surface for reference subtraction. Final data of each interaction was deducted from reference channel and buffer channel data. The experimental data was fitted by steady state affinity mode and shown in Table 5 below.

TABLE 5

| FcRn binding | |
| --- | --- |
| Ligand | KD (M) |
| Ab#D | 2.25E−06 |
| Ab#H | 2.61E−06 |
| Ab#L | 2.60E−06 |
| Ab#P | 2.55E−06 |
| Ab#T | 2.56E−06 |

All antibodies showed similar FcRn binding which is desirable.

D. Binding to C1q by ELISA

Plates (Nunc) were coated with antibodies at 3 μg/mL overnight at 4° C. After blocking and washing, C1q was half-log titrated in blocking buffer (600, 189.75, 60.01, 18.98, 6.00, 1.90, 0.60, 0.19, 0.06 and 0.02 μg/mL) and incubated at room temperature for 2 h. The plates were then washed and subsequently incubated with secondary antibody Sheep anti-human C1q Ab-HRP for 1 h. After washing, TMB substrate was added and the interaction was stopped by 2M HCl. The absorbance at 450 nm was read using a microplate reader (Molecular Device) and shown in Table 6 below.

TABLE 6

| C1q binding | |
| --- | --- |
| Antibody | KD |
| Ab#D | 75 nM |
| Ab#H | no binding |

TABLE 6-continued

| C1q binding | |
| --- | --- |
| Antibody | KD |
| Ab#L | weak binding |
| Ab#P | no binding |
| Ab#T | no binding |

All antibodies showed low or no C1q binding which is advantageous.

Example 3. Epitope Mapping

To reconstruct epitopes of the target molecule a library of peptide based epitope mimics was synthesized using solid-phase Fmoc synthesis. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer).

Synthesis of structural mimics was done using Chemically Linked Peptides on Scaffolds (CLIPS) technology. CLIPS technology allows to structure peptides into single loops, double loops, triple loops, sheet-like folds, helix-like folds and combinations thereof. CLIPS templates are coupled to cysteine residues. The side-chains of multiple cysteines in the peptides are coupled to one or two CLIPS templates. For example, a 0.5 mM solution of the P2 CLIPS (2,6-bis(bromomethyl)pyridine) is dissolved in ammonium bicarbonate (20 mM, pH 7.8)/acetonitrile (1:3 (v/v)). This solution is added onto the peptide arrays. The CLIPS template will bind to side-chains of two cysteines as present in the solid-phase bound peptides of the peptide-arrays (455 wells plate with 3 μl wells). The peptide arrays are gently shaken in the solution for 30 to 60 minutes while completely covered in solution. Finally, the peptide arrays are washed extensively with excess of $H_2O$ and sonicated in disrupt-buffer containing 1% SDS/0.1% 2,2'-(Ethylenedioxy)diethanethiol in PBS (pH 7.2) at 70° C. for 30 minutes, followed by sonication in $H_2O$ for another 45 minutes. The T3 CLIPS carrying peptides were made in a similar way but now with three cysteines.

Different sets of peptides were synthesized according to the following designs. Note that actual order of peptides on mini-cards in some was randomized.

| | Set 1 | Set 2 |
| --- | --- | --- |
| Label | RN.FLSRPTEKTI | WN |
| Description | Single residue substitution variants derived from the lead sequence FLSRPTEKTI. In this series every residue within the peptide is replaced by all other proteogenic residues with an offset of one residue. | Peptides of length 5, 6, 7, 8 and 9 derived from the lead peptide sequence FLSRPTEKTI with an offset of one residue. |

-continued

| | Set 1 | | Set 2 | |
|---|---|---|---|---|
| Sequences | FWSRPTEKTI | (SEQ ID NO. 20) | FLSRP | (SEQ ID NO. 30) |
| (first 10) | FLSRPTEKTC | (SEQ ID NO. 21) | LSRPT | (SEQ ID NO. 31) |
| | FLGRPTEKTI | (SEQ ID NO. 22) | SRPTE | (SEQ ID NO. 32) |
| | FLSRPTEKDI | (SEQ ID NO. 23) | RPTEK | (SEQ ID NO. 33) |
| | FLSRPTEKYI | (SEQ ID NO. 24) | PTEKT | (SEQ ID NO. 34) |
| | FLSRWTEKTI | (SEQ ID NO. 25) | TEKTI | (SEQ ID NO. 35) |
| | FLSRPSEKTI | (SEQ ID NO. 26) | FLSRPT | (SEQ ID NO. 36) |
| | FLNRPTEKTI | (SEQ ID NO. 27) | LSRPTE | (SEQ ID NO. 37) |
| | FLSRPFEKTI | (SEQ ID NO. 28) | SRPTEK | (SEQ ID NO. 38) |
| | FLSRPTEKTG | (SEQ ID NO. 29) | RPTEKT | (SEQ ID NO. 39) |

The binding of antibody to each of the synthesized peptides was tested in ELISA. The peptide arrays were incubated with primary antibody solution (overnight at 4° C.). After washing, the peptide arrays were incubated with a 1/1000 dilution of an appropriate antibody peroxidase conjugate (SBA; goat anti-human HRP conjugate, Southern Biotech) for one hour at 25° C. After washing, the peroxidase substrate 2,2'-azino-di-3-ethylbenzthiazoline sulfonate (ABTS) and 20 µl/ml of 3 percent $H_2O_2$ were added. After one hour, the color development was measured. The color development was quantified with a charge coupled device (CCD)—camera and an image processing system.

The values obtained from the CCD camera range from 0 to 3000 mAU, similar to a standard 96-well plate ELISA-reader. The results are quantified and stored into the lab database. Occasionally a well contains an air-bubble resulting in a false-positive value, the cards are manually inspected and any values caused by an air-bubble are scored as 0.

To verify the qualify of the synthesized peptides, a separate set of positive and negative control peptides was synthesized in parallel. These were screened with commercial antibodies 3C9 and 57.9 (ref. Posthumus el al. (1990) J. Virol. 64:3304-3309).

A graphical overview of the complete dataset is given in FIG. 1. Here a box plot depicts each dataset and indicates the average ELISA signal, the distribution and the outliers within each dataset. Depending on experiment conditions (amount of antibody, blocking strength, etc.) different distributions of ELISA data are obtained. Specifically, the bottom and top of the boxes are the 25th and 75th percentile of the data. The band near the middle of the box is the 50th percentile (the median). The whiskers are at 1.5 the inter-quantile range, an indication of statistical outliers within the dataset (Mcgill et al., (1978) The American Statistician, 32: 12-16).

Figure 2:
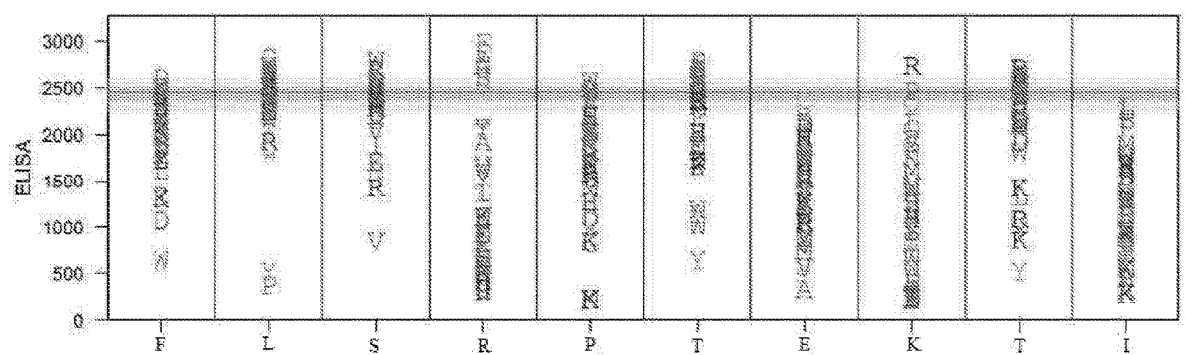
FIG. 2. Letterplot graph of a full substitution analysis of peptide FLSRPTEKTI (SEQ ID NO: 19) probed with antibody under high stringency conditions. The base sequence is listed below the graph, mean signal for the base sequence is at the red line. Substitutions at a given position are plotted at the signal intensity recorded for that replacement.
Figure 3:
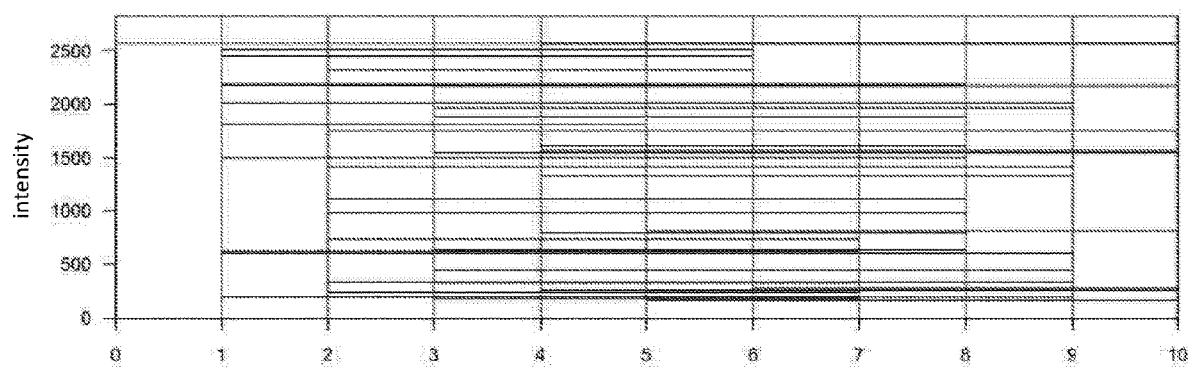
FIG. 3. Letterplot graph of a full substitution analysis of peptide FLSRPTEKTI (SEQ ID NO: 19) probed with antibody under high stringency conditions. The base sequence is listed below the graph, mean signal for the base sequence is at the red line. Substitutions at a given position are plotted at the signal intensity recorded for that replacement.

Antibody was tested under high stringency conditions at a high concentration. Recorded results are depicted in FIG. 2 and FIG. 3. Data for each of two peptide sets was analyzed separately.

Analysis of data recoded with substitution variants of the lead sequence FLSRPTEKTI (SEQ ID NO: 19) suggested that many replacements of either residue within the sequence negatively, although to a differing degree, impact binding of the antibody (FIG. 2). Only one exception was seen-residue L2, which does not tolerate L2P and L2Y replacements, but remains insensitive to all other replacements.

Analysis of data recorded with truncation variants of the lead sequence FLSRPTEKTI (SEQ ID NO: 19) indicated that the N-terminus of the sequence is preferred by the antibody (FIG. 3). Many constructs derived from the central part of FLSRPTEKTI (SEQ ID NO: 19) are also well recognized. In summary, the antibody was tested on a peptide array comprised of two types of peptide variants derived from the lead sequence FLSRPTEKTI (SEQ ID NO: 19)—single residue mutants and truncation variants. The antibody yielded detectable binding under high stringency conditions. Many replacements throughout FLSRPTEKTI (SEQ ID NO: 19) were unfavorable for the antibody. The antibody was stronger binding truncation constructs derived from the N-terminal part of the sequence.

Example 4. Antibody Stability

Antibody stability is an important factor affecting development, efficacy, production cost, etc. After sequence optimization, key stability parameters were evaluated. The species distribution profiles of various antibodies under acidic and heat conditions were tested. All antibodies show improved stability.

A. SE-UPLC (Size-Exclusion Ultra Performance Liquid Chromatograph)
  Formulation: PBS, pH 6.5 or 7.2
  Concentration (mg/mL): 5.28, 5.13, 5.00, 5.17, 5.01, 5.26, 4.92, 5.04, 4.99, 5.12 (all at about 5 mg/mL)
  Condition: room temperature, acidic treatment then storage at 4° C. for 1 week or at 40° C. for 1 week
  2 µL of sample was injected into ACQUITY UPLC Protein BEH SEC 200, 1.7 µm, 4.6×150 mm column with a flow of 0.3 mL/min for 10 minutes. A mobile phase of 50 mM Sodium Phosphate, 500 mM NaCl, pH 6.2 was used. All antibodies show desirable stability under various pH, heat and storage conditions.

B. rCE-SDS (Reduced Capillary Electrophoresis-Sodium Dodecyl Sulfate)
  Formulation: PBS, pH 6.5, 7.2, 6.2
  Concentration (mg/mL): 0.5
  Condition: room temperature, acidic treatment then storage at 4° C. for 1 week or at 40° C. for 1 week
  The sample was prepared in reducing labeling buffer before being submitted to the LabChip GXII system (PerkinElmer). All antibodies show desirable stability under various pH, heat and storage conditions.

Example 5. Assays for Hemichannel Opening

A. In Vitro Assays
  The antibodies disclosed herein can be tested in vitro for their effect on hemichannel opening using a dye-uptake assay. The dye can be a fluorescent tracer dye (e.g., ethidium bromide or Lucifer yellow).
  In one example, a fluid flow loop apparatus (FFLA) (Parrallel Plate Flow Chamber), or modification thereof, can be used. FFLA mimics dynamic fluid microenvironment in the bone to produce fluid flow shear stress (FFSS). Cells are cultured in a parallel plate flow chamber, exposing the cells to steady laminar fluid flow.

Osteocytes sense mechanical strain produced by FFSS in the osteocyte lacuna/canalicular network. It has been proposed that bone fluid flow is driven by extravascular pressure as well as applied cyclic mechanical loading of osteocytes and that the peak physiologic loads are 8 to 30 dyn/cm$^2$. In certain aspects FFSS levels were in range of physiological values reported from previous studies measuring fluid flow within bone. Fluid shear stress magnitude can be changed by adjusting column height of the flow loop.

Assays used to assess the functionality of the hemichannels can use a fluorescent tracer molecule that is small enough to pass through the pore of the hemichannel. If the hemichannel is closed the molecules cannot pass. If the hemichannel is open the dye can pass through and cause the cell to fluoresce, allowing quantification of the fluorescence. When ethidium bromide attaches to DNA it becomes fluorescent. Lucifer yellow fluoresces once it is located inside of a cell.

Dye transfer methods can comprise exposing cells to extracellular fluorescent permeability tracers. Extracellular permeability tracers are molecules that remain outside of cell unless some condition increases the permeability of the cell membrane. In certain aspects the tracers have a mass of less than 1, 2, or 3 kDa. In other aspect the tracer will have a net charge. Such permeability tracers include, but are not limited to the anionic dyes Lucifer yellow (LY; net charge=−1) and cationic probes ethidium bromide (Etd; net charge=+1), propidium iodide (PI; net charge=+2). The fluorescence of EtBr is enhanced upon binding to DNA, increasing the contrast and allowing more easy identification. In certain aspects extracellular dye is removed at different time periods or after the application of stimuli to open hemichannels and the fluorescence intensity retained by each cell is quantified. In certain aspects fluorescence intensity is quantified in snap shot images.

The materials used in in vitro assays to test hemichannel opening include:

Hemichannel expressing cells or cell lines. Cells or cell lines expressing the various connexin hemichannels can be obtained, isolated, or engineered using methods and/or expression vectors known in the art.

Osteocytes: Primary osteocytes isolated from animals (including mouse, rats, rabbits, chicken) etc. or osteocytic cell lines including, but not limited to MLO-Y4 cells and others.

Cancer cells: Breast cancer cell lines: including ER, PR, HER and TP53 positive/negative cells (e.g., MD-MBA-231, MCF7, T47D, or ZR751). MDA-MB-231 is mammary gland ductal carcinoma. Py8119 mammary tumor cell lines were established from spontaneous mammary tumors arising in C57Bl/6 MMTV-PyMT females (mouse mammary tumor virus promoter-driven polyoma middle T transgene) mice. The expression of the oncogene (polyoma middle T transgene) is driven by the Mouse Mammary Tumor Virus promoter Prostate cancer cell lines: including androgen receptor and 5α-reductase positive/negative and androgen sensitive/insensitive cell lines (e.g., LNCaP-Rf, BM18, pRNA-1-1/ras, RC58T/hTERT, PPC-1, etc).

Osteoblasts: MLO-A5 osteoblasts are used as a control because they express Connexin 43, but they do not appear to open when stimulated by alendronate.

Tracer Molecules include, but are not limited to lucifer yellow, ethidium bromide, Evans Blue, Alexa350, Alexa488 and Alexa594.

Cr43(E2): The Cx43(E2) antibody is specific for Cx43 hemichannels. Cx43E2 binds the $2^{nd}$ extracellular loop of Cx43 hemichannels and prevents hemichannel opening.

Methods for determining if an antibody opens hemichannels include one or more of the following steps:

(a) Isolating, obtaining, or producing a connexin expressing cell or cell line. For example, primary osteocytes can be isolated from calveria. Other cell types can be isolated using other methods known in the art. In certain aspects calvarial osteocytes are isolated from animals (e.g., 16-day embryonic chicken calvaria or new-born mice). Animals are decapitated and calvarial bone is dissected and quickly dipped in 70% alcohol. The calvarial bone is then put in αMEM and washed multiple times with PBS. Cleaned bones are placed in fresh αMEM. The bones are minced and cut into 1.5 mm area size. The bone pieces can be treated with collagenase to remove soft tissues and osteoid followed by decalcificahon using EDTA. Finally, osteocytes are released from the bone chips by treating with collagenase and vigorous agitation.

(b) Isolating primary osteocytes from long bone. Long bone osteocytes can be isolated from 2-3 week old mice or rats. For example, mice are given an overdose of anesthesia, and cervically dislocated, decapitated, and dipped into 70% Ethanol. The femur and tibia with the end of the joints still intact are isolated. The leg is quickly dipped in 70% alcohol and then placed into αMEM. Legs in αMEM are washed with PBS. The major portion of muscle is removed, and detached from the tendons/ligaments. Cleaned bones are placed in fresh αMEM. Once all bones are cleaned, both ends of each bone are cut off using a scalpel just prior to flushing out the marrow using PBS. Bones are cut into 1.5 to 2 mm lengths and treated with collagenase. In one example, the bone pieces are treated with collagenase sequentially 9 times to remove all other tissues and osteoid followed by decalcification using EDTA.

(c) Culturing the cells or cell lines. For example, primary and/or osteocytic cell lines are cultured on collagen-coated plates and are bathed in recording medium ($HCO_3$-free α-MEM medium buffered with HEPES) containing a permeability tracer.

(d) Administering a test antibody. The cultured cells are placed contacted with a test antibody for desirable amount of time.

(e) Determining permeability tracer uptake. Permeability tracer uptake is determined by detecting the amount of tracer inside the cells. In certain aspects time-lapse recording is used. Fluorescence can be recorded at regions of interest in different cells with an eclipse filter on a microscope based on the wavelength of the fluorescence of the tracer or other probe(s) being used. In certain aspects images are captured by fast cooled digital camera every 2 minutes and image processing is performed with ImageJ software. The collected data can be illustrated as fold difference of initial fluorescence and fluorescence at the time of interest versus the basal fluorescence.

For snapshot images, cells can be exposed to permeability tracer for 5-10 minutes, rinsed multiple times with PBS, and fixed with formaldehyde. In certain aspects, at least three microphotographs of fluorescence fields are taken with a microscope. Image analysis is done with ImageJ software. The average of pixel density of random cells is measured.

Confirmation of the opening of connexin hemichannels can be obtain by, for example, incubating osteocytes with Cx43(E2) antibody, a polyclonal antibody specifically-inhibiting Cx43 hemichannels, along with the test antibody. If the test antibody opens Cx43 hemichannel, this channel opening will be blocked by Cx43(E2) antibody. To control for the opening of Cx43 hemichannels, osteocytes are treated with fluid flow shear stress and/or AD, both known to open hemichannels in osteocytes.

In a particular example, MLO-Y4 osteocytic cells were treated with 20 µM AD or a test antibody for 30 min in the absence or presence of 1 µg/ml Cx43(E2) antibody. Ethidium bromide dye uptake was conducted and quantified as compared to non-treated basal level of uptake. The assay was carried out in presence of calcium. Low calcium conditions can be used as control (opens hemichannels). The opening of osteocytic hemichannels induced by AD or a test antibody is blocked by Cx43(E2) antibody.

B. In Vivo Assays

In certain aspects Cx43 modulation in osteocytes is determined by injecting candidate reagents into a long bone and using fluorescence tracer dyes (e.g., calcein or Evans blue) to detect the opening of hemichannels in osteocytes in situ.

One example of an in vivo assay to analyze hemichannels in osteocytes uses 3-4 month old mice or rats. The animals are weighed. A test antibody is introduced into the animal through intraperitoneal (IP) injection. After 2-4 hours, fluorescence tracer dyes (i.e. Evans blue, Alexa 594) are injected into lateral tail vein of the animal or by IP injection. Note: up to 1% of animal's body weight in volume can be injected. In certain aspects the animal is warmed prior to tail vein injection to dilate the tail vein. After 2-4 hours, the animal is scarified and tibial and femur bones free of muscle tissues are dissected and washed multiple times with PBS. The bone is fixed in paraformaldehyde and decalcified in 14% EDTA solution at 4° C. for two weeks or room temperature under constant agitation for 3-5 days. The bone is washed in PBS and soaked in 30% sucrose in PBS overnight and embedded in OCT compound. Position of the bone is typically adjusted in the mold as needed. Five µm thick frozen sections are cut using a cryostat, the sections rinsed in PBS, and mounted using 50% glycerol in PBS. The bone sections can be examined under fluorescence microscope and the degree of osteocytes in the bone taking up tracer dyes are quantified using Image J.

The opening of Cx43 hemichannels in osteocytes can be confirmed by mechanical loading on tibias opening Cx43 hemichannels in osteocytes. This can serve as a positive control for hemichannel opening in osteocytes in vivo. For negative control, mice with the deficiency of Cx43 in osteocytes are used. This mouse is generated by crossing with 10-kb DMP-1 Cre and Cx43 flox mice.

Example 6. Assays for Cancer Cell Migration, Viability and Metastasis

A. In Vitro Assays

Assays for cancer cell migration. Cx43 hemichannels in osteocytes are opened by administration of AD or FFSS. The opened hemichannels permit the release of various factors into the medium producing a conditioned medium (CM). The released factor(s) in the AD- or FFSS-treated CM decrease cancer cell migration as determined by soft agar and wound healing assays. Cancer cells treated with control CM exhibit normal migration. The soft agar assay is an assay for anchorage-independent growth, as contrasted with anchorage-dependent growth. Only cancer cells can grow on soft agar and their growth on this matrix indicates the extent of the cancer cell proliferation.

In certain embodiments cancer (e.g., breast or prostate) cells are incubated with CM and cancer cell proliferation, migration, and invasion are determined.

Cancer cell growth and viability can be determined using WST-1 (Water Soluble Tetrazolium salts) assay, viable cell counting using Trypan blue method, BrdU DNA incorporation, and cell proliferation assay. For WST-1 assay, the cell proliferation is measured at an emission wavelength of 450 nm with a Synergy HT Multi-Mode Microplate Reader (Biotek).

Cell migration assays are typically performed in transwell membrane filter inserts in 24-well tissue culture plates (BD Biosciences). The transwell membrane filter inserts can be, for example, 6.5-mm diameter, 8-µm pore size, and 10-nm thick polycarbonate membranes.

Invasion assays are performed in BD Biocoat Growth Factor Reduced Matrigel Invasion Chambers (BD Biosciences). The cancer cell lines are harvested and resuspended in CM from osteocytes with or without the test antibody. Cancer cell suspensions are added to the upper side of the inserts. Cells are incubated at 37° C. for various periods of time. Cells that do not migrate through the filters are removed, and cells that migrate through the inserts are fixed and stained with Hema 3 Stat Pack (Fisher Scientific). The number of migrated cells in 5 fields of view per insert is counted under a light microscope.

Breast cancer cell migration can be decreased when incubated in CM from osteocytes treated with AD or FFSS or the antibodies disclosed herein to stimulate Cx43 hemichannel opening. When osteocyte Cx43 hemichannels were blocked by E2 antibody, this inhibitory effect on cancer cell migration was attenuated. This decrease in cancer cell migration is not seen when incubated with CM collected from osteoblasts or when treated directly with AD. Opening of Cx43 hemichannels by the antibodies disclosed herein is protective against breast cancer cell growth and migration.

B. In Vivo Assays

The effect of the test antibody on bone metastasis in vivo is determined using an intratibial injection bone metastasis model and/or intracardiac injection cancer metastasis assay.

Intratibial injection bone metastasis model. The method includes anesthesizing 1-month old, normal or immunocompromised mice using isoflurane. The mice are also given buprenorpine-HCl (0.3 mg/ml) as an analgesic. Intratibial injections are performed using cancer cells expressing fluorescence or chemiluminescence markers (e.g., Py8119 cells expressing Luc-GFP to normal mice or Luc-GFP-expressing MD-MBA-231 to immunocompromised mice). The cancer cells are inoculated into the bone marrow area of right tibias through a pre-made hole made by a Hamilton syringe fitted with a 30-gauge needle. PBS was injected into the left tibias as control. The test antibody or saline is administered IP twice a week for 5 weeks. Intratibial tumor growth is monitored with bioluminescence imaging or fluorescence every week starting from 3 days after tumor cell inoculation. At the termination of the study after sufficient bioluminescence imaging, X-ray images are taken to test bone quality and labeled metastatic cancer cell colonies are observed and counted with a fluorescence microscope.

Intracardiac injection bone metastasis model. Two-three month old, normal or immunocompromised mice are anesthetized by isoflurane and are also given buprenorpine-HCl (0.3 mg/ml) as an analgesic. Cancer cells expressing fluorescence or chemiluminescence markers (e.g., Py8119 cells expressing Luc-GFP to normal mice or Luc-GFP-MD-MBA-231 to immunocompromised mice) are injected into the left cardiac ventricle of mice. The procedure includes: Holding the needle angled towards the operator and to the right, insert it into the second intercostal space, approximately 3 mm to the left of the sternum. Advance about 5 mm and turn the needle gently until the pulsatile flow of bright red arterial blood is observed entering the hub. Inject the cell suspension over 30 sec. Withdraw the needle and apply pressure on the injection site for 30 sec using an alcohol wipe. Place the mouse on a warmed surface until it has fully recovered from anesthesia. Perform bioluminescent or fluorescent imaging after intracardiac injection to verify distribution of tumor cells every week from 3 days after tumor cell inoculation. At the termination of the study after sufficient bioluminescence imaging, X-ray images are taken to assess bone qualify and labeled metastatic cancer cell colonies are observed and counted with a fluorescence microscope.

Cx43 conditional knock out (cKO) mice. Because homozygous Cx43 global knockouts are lethal, and also because the inventors want to examine the role of Cx43 expressed in osteocytes, osteocyte-specific Cx43 knockout mice were generated. Crossing mice homozygous for the floxed Cx43 gene with Cx43 global heterozygous mice to facilitate the complete deletion of Cx43 in osteocytes. Cx43fl/− mice (50% of progeny) were then crossed with mice expressing Cre recombinase driven by the human DMP-1 promoter. This created mice that were Cx43 fl/−, DMP1 Cre+ or Cx43 fl/−, DMP1 Cre-(small percentage are Cx43fl/fl or Cx43−/−). Cx43 deficient osteocytes were confirmed by immunohistochemistry.

Studies can include 8 groups of mice: WT treated with alendronate (AD), WT without AD, cKO treated with AD, cKO without AD, WT treated with test antibody (TA), WT without TA, cKO treated with TA, and cKO without TA. AD or TA was administered to the mice at 150 μg/kg body weight. With AD or TA treatment it is expected bone metastasis will increase in KO compared to WT mice. And without AD or TA treatment bone metastasis should be similar between WT and knockout mice.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

The invention claimed is:

1. An anti-Cx43 antibody, or antigen binding fragment thereof, comprising: a first, second and third heavy chain complementarity determining region (CDR) sequence having the amino acid sequence of SEQ ID NOs: 1, 2, and 3, respectively; and a first, second and third light chain CDR sequence having the amino acid sequence of SEQ ID NOs: 4, 5, and 6, respectively;
wherein the antibody or fragment thereof comprises a heavy chain variable domain having the amino acid sequence having at least 95% sequence identity to SEQ ID NO: 7, and a light chain variable domain having the amino acid sequence having at least 95% sequence identity to SEQ ID NO: 8.

2. The antibody or fragment thereof of claim 1, comprising a heavy chain variable domain having the amino acid sequence of SEQ ID NO: 7, and a light chain variable domain having the amino acid sequence of SEQ ID NO: 8.

3. An anti-Cx43 antibody, or antigen binding fragment thereof, comprising a heavy chain having an amino acid sequence selected from the group consisting of SEQ ID NOs: 9-17, and a light chain having the amino acid sequence of SEQ ID NO: 18.

4. An anti-Cx43 antibody, or antigen binding fragment thereof of claim 1, wherein, when bound to Cx43, binds to an epitope located within the amino acid sequence of FLSRPTEKTI (SEQ ID NO: 19).

5. The antibody or fragment thereof of claim 4, wherein the epitope comprises one or more amino acids selected from the group consisting of F1, S3, R4, P5, T6, E7, K8, T9 and 110 of SEQ ID NO: 19.

6. The antibody or fragment thereof of claim 4, wherein the epitope consists of F1, S3, R4, P5, T6, E7, K8, T9 and 110 of SEQ ID NO: 19.

7. The antibody or fragment thereof of claim 4, wherein the epitope comprises all ten amino acids of SEQ ID NO: 19.

8. The antibody or fragment thereof of claim 4, wherein the epitope consists of all ten amino acids of SEQ ID NO: 19.

9. The antibody or fragment thereof of claim 1, which promotes opening of Cx43 hemichannels in osteocytes.

10. A pharmaceutical composition comprising the antibody or fragment thereof of claim 1 and a pharmaceutically acceptable carrier.

11. A pharmaceutical composition comprising the antibody or fragment thereof of claim 4 and a pharmaceutically acceptable carrier.

* * * * *